United States Patent
Peabody et al.

(10) Patent No.: US 6,758,975 B2
(45) Date of Patent: Jul. 6, 2004

(54) AUTOMATED PERITONEAL DIALYSIS SYSTEM AND PROCESS WITH IN-LINE STERILIZATION OF DIALYSATE

(75) Inventors: Alan M. Peabody, Greenville, SC (US); Jeffrey J. Shimon, Mountain View, CA (US); Joel Frederic Jensen, Redwood City, CA (US)

(73) Assignee: Piedmont Renal Clinic, PA, Greenville, SC (US)

( * ) Notice: Subject to any disclaimer, the term of this patent is extended or adjusted under 35 U.S.C. 154(b) by 89 days.

(21) Appl. No.: 10/075,175

(22) Filed: Feb. 14, 2002

(65) Prior Publication Data

US 2002/0162778 A1 Nov. 7, 2002

Related U.S. Application Data

(60) Provisional application No. 60/269,570, filed on Feb. 16, 2001.

(51) Int. Cl.[7] ............................................. B01D 65/02
(52) U.S. Cl. .............................. 210/645; 73/38; 73/40; 210/85; 210/90; 210/257.2; 210/321.69; 210/739; 210/741; 604/29; 604/65
(58) Field of Search ........................... 210/85, 90, 97, 210/106, 108, 257.2, 258, 321.69, 321.71, 636, 645–647, 739, 741, 744; 73/38, 40, 40.5 R, 40.7; 134/22.1, 22.11, 22.12, 56 R; 604/29–31, 65, 4.01, 5.01

(56) References Cited

U.S. PATENT DOCUMENTS

| | | | |
|---|---|---|---|
| 3,825,493 A | 7/1974 | Brown et al. | 210/23 |
| 4,239,041 A | 12/1980 | Popovich et al. | 128/213 |
| 4,311,587 A | 1/1982 | Nose et al. | 210/136 |
| 4,311,687 A | 1/1982 | Hertl et al. | 210/136 |
| 4,586,920 A | 5/1986 | Peabody | 604/29 |
| 4,718,890 A | 1/1988 | Peabody | 604/29 |
| 4,747,822 A | 5/1988 | Peabody | 604/29 |
| 5,004,459 A | 4/1991 | Peabody et al. | 604/29 |
| 5,643,201 A | 7/1997 | Peabody et al. | 604/31 |
| 5,683,584 A | 11/1997 | Wenthold et al. | 210/500 |
| 5,808,181 A * | 9/1998 | Wamsiedler et al. | 73/38 |
| 5,827,820 A * | 10/1998 | duMoulin et al. | 514/2 |
| 5,925,011 A * | 7/1999 | Faict et al. | 604/29 |
| 5,944,684 A | 8/1999 | Roberts et al. | 604/5 |
| 6,074,559 A | 6/2000 | Hahmann et al. | 210/645 |
| 6,254,567 B1 * | 7/2001 | Treu et al. | 604/29 |
| 6,280,632 B1 * | 8/2001 | Polaschegg | 210/739 |
| 6,635,179 B1 * | 10/2003 | Summerton et al. | 210/650 |

* cited by examiner

*Primary Examiner*—Joseph Drodge
(74) *Attorney, Agent, or Firm*—McNair Law Firm, PA; Cort Flint

(57) ABSTRACT

An automated peritoneal dialysis system for performing continuous peritoneal dialysis is disclosed which includes a fluid circuit for delivering unsterilized dialysate from an uninterrupted supply, and a dialysate sterilization component having at least one in-line sterilization filter assembly disposed in the inflow line segment for realtime sterilization of the unsterilized dialysate during flow prior to patient delivery. A filter test component is operatively associated with the sterilization filter assembly for conducting a real-time integrity test on the filter assembly to test for a filter failure which would allow contaminants into the dialysate prior to patient delivery. If the filter fails the test, the fluid is discarded. In this manner, sterilization of fluid in realtime during a peritoneal dialysis process provides a high rate of dialysate exchange during repeated dialysate fill and drain cycles.

64 Claims, 6 Drawing Sheets

AUTOMATED PERITONEAL DIALYSIS SYSTEM AND PROCESS WITH IN-LINE STERILIZATION OF DIALYSATE

This application claims the benefit of provisional application 60/269,570, filed on Feb. 16, 2001.

FIELD OF THE INVENTION

The invention relates to an automated peritoneal dialysis system and process that provides a large supply of proportioned dialysis fluid which is used in a peritoneal dialysis system and process wherein the dialysis fluid is sterilized in-line with integrity checks in realtime during dialysis before delivery to a patient's peritoneal cavity.

BACKGROUND OF THE INVENTION

The National Institute of Health (NIH) reports that more than 289 people per million population in the United States require renal replacement therapy in the form of dialysis. The main barriers to treating dialysis patients have been expense and practicality. Moreover, the largest portions of the world's population live in countries that do not support dialysis. Patients in those areas who need dialysis must pay for their own treatment, which leads to a sparing use of material that results in serious under dialysis and ineffective treatment. In the United States, the need for the patient to drive to a dialysis center for treatment, often over long distances, is a serious barrier to obtaining dialysis treatment for some needy patients. It is rather impossible to provide in-center dialysis to patients who cannot get to the clinic. Furthermore, in countries where there are few dialysis patients there is no highly trained and dedicated staff to care for the patients' special needs. In short, the high cost of the current dialysis methods, massive supplies that must be delivered and stored for home dialysis, inadequate transportation, and a lack of trained professional healthcare workers capable of delivering dialysis treatment, are serious obstacles for dialysis patients.

There are two methods of clinical dialysis in widespread use today. They are called hemodialysis and peritoneal dialysis. They differ in the method by which the patient's blood is exposed to the dialysate. Hemodialysis is the most widely used type of clinical dialysis. In this method, the patient's blood is taken outside the body and passed through a dialysis cell, called a hemodialyzer. The hemodialyzer includes a membrane. The patient's blood flows on a sterile side of the membrane while the dialysate flows along the opposite side. Dialysis of blood toxins and excess water occurs across the membrane. U.S. Pat. Nos. 5,683,584 and 6,074,559 disclose typical blood filters for use in hemodialysis to filter blood. This process requires the assistance of trained personnel and subjects the patient to life threatening dangers of mechanical malfunction, rapid shifts of fluid and metabolite, and surgery associated with attaching an artery directly to a vein to produce an adequate blood flow for dialysis treatment. Hemodialysis removes excess fluid from a patient by a process called ultrafiltration, which uses hydrostatic pressure to force water out of the blood, across the hemodialyzer, and into the dialysate for removal. It is also known to reuse blood filters after hemodialysis and to test the filter membrane when it is fully wetted with an aqueous solution using pressurized air to determine if there is a leak in the filter membrane, such as disclosed in U.S. Pat. No. 5,808,181.

Peritoneal dialysis was developed as a means of surmounting some of the difficulties associated with in-center hemodialysis. In addition, peritoneal dialysis is more suitable for in home use. In peritoneal dialysis, a specially prepared, sterilized dialysis fluid (dialysate) is instilled into the peritoneal cavity through an in-dwelling dialysis catheter. The toxins move down the gradient and into the dialysate, freeing the body of toxins. The dialysate is allowed to remain in the peritoneal space for a period, commonly called the dwell time, in order to maximize the quantity of toxins removed per unit volume of dialysate. Then, after absorbing body toxins in a long slow process, the dialysis fluid is removed and discarded. The longer the fluid remains in the cavity the less effective it becomes at removing waste due to the shift in the gradient towards equilibrium. The process is then repeated until the level of toxic metabolites in the blood is reduced to a desired level. This method is commonly referred to as the "intermittent" or "batch" method due to the fact that multiple one or two liter bags of fresh, sterilized dialysis solution must be constantly exchanged to provide the supply of fresh, sterilized dialysate with an acceptable osmotic gradient. Peritoneal dialysis uses an osmotic gradient that is created by adding an osmol, usually glucose, to the dialysate to remove the patient's excess fluid.

Commercially available, pre-sterilized peritoneal dialysate is expensive. Most patients have a peritoneal dialysis prescription of ten to fifteen liters per session, five to six times a week. However, this volume of fluid is frequently inadequate for the patient's need but is all the patient can afford. The home peritoneal patient must have a large storage space in which to put the dialysis solution he will need until the next monthly shipment. On average, they must have the capacity to store about seventy-five to ninety gallons of dialysate to last the month. In addition, the patients must keep on hand a supply of other dialysis solutions with different glucose levels to meet changing body conditions.

Infection is one of the greatest dangers of peritoneal dialysis, either at home or in the hospital. Each time a sterile seal is broken, there is the danger of introducing bacteria into the system. Thus, each time a patient inserts a tube in a bag of fluid, or connects the tubing to his own in-dwelling catheter, or attaches the drainage bag, or does anything else which opens the system, there is the potential for contaminating the system and threatening the life of the patient. The more times the system must be opened, the greater the danger of contamination. The danger is actually compounded by fatigue, physical incapacity, and carelessness. The more often the patient must open the system, the less careful he becomes with each instance.

To overcome the above problems, various automated processes and systems for peritoneal dialysis have been proposed which seek to overcome the problems associated with the "batch" method of peritoneal analysis. For example, U.S. Pat. Nos, 4,586,920, 4,718,890, 4,747,822, 5,004,459, and 5,643,201, issued to the present inventor, all relate to continuous or cyclic peritoneal dialysis systems and processes for overcoming the problems associated with effective home dialysis for needy patients. U.S. Pat. Nos. 4,586,920, 4,718,890, and 4,747,882 disclose single and double catheter peritoneal dialysis systems and methods which are automated in a continuous and cyclic manner. A reverse osmosis unit in combination with various filters produces sterilized water which is mixed with a dialysate in a conventional proportioning machine to produce a properly mixed dialysis solution. The dialysis solution is delivered through a high volume bacterial filter which sterilizes the dialysis solution. The sterilized dialysis solution is then stored in a head vessel for use in subsequent dialysis process. To test for sterilization, the dialysis solution may be cultured in the head vessel to see if a bacteria grows. U.S. Pat. No. 5,004,459 discloses an automated cyclic peritoneal dialysis system and process which automatically adjusts the osmoality of the dialysis fluid in response to the amount of excess fluid removed from the patent. Sterilized dialysis fluid is provided by mixing sterilized water and dialysate concentrate in a sterilized preparation unit. The dialysis preparation unit is disposed upstream of the dialysis machine which has been pre-sterilized with bleach or the like. U.S. Pat. No. 5,643,201 discloses an automated cyclic-tidal peritoneal dialysis system and process having a reverse osmosis unit for sterilizing water with a concentrate dialysate to produce a proportioned dialysis solution whereupon the dialysis solution is further sterilized by heating, and stored in a reservoir before use in the system and process. These prior systems and processes have mainly been directed to the provision of automatic control systems and processes having suitable controllers, valves, flow monitors, and pressure monitors to insure the dialysis process is safe for the patient. Emphasis has not been placed on providing an adequate, realtime source of sterilized dialysis fluid in an automated, peritoneal system and process which is closed. The provision of an adequate preparation and supply system for sterilized dialysis fluid in an automated peritoneal system and process for effective in home use has remained a problem. Since the intended use of a continuous or cyclic flow system is in a patient's home, beyond the supervision of trained medial personnel, it is of primary importance that every effort be made to sterilize the system and fluids to protect the patient. Thus, given the present state of the art, there is a need for improvement.

Accordingly, an object of the present invention is to provide an automated peritoneal dialysis system and process wherein the dialysis fluid is reliably sterilized to provide a generally continuous supply of sterile dialysis fluid available on demand in a quick, simple, cost efficient manner.

Another object of the present invention is the provision of a generally continuous supply of sterilized dialysis solution for use in an automated peritoneal dialysis process wherein sterilization is achieved realtime in the flow line during the process and prior to patient entry in a reliable manner.

Another object of the present invention is to provide an automated cyclic peritoneal dialysis system and process using a flow-line sterilization filter and process which includes an integrity check for the filter to reduce the possibility of bacteria and other contaminants entering the patient's peritoneal cavity.

Another object of the present invention is to provide an automated peritoneal dialysis system and process that adjusts the osmolality of the dialysate to achieve the prescribed amount of fluid removal best suited for the patient without having to switch between various bags of dialysate with different concentrations while sterilizing fluid as it is delivered to the patient, and to minimize the overall number of patient connections in the system.

Another object of the present invention is to provide a continuous peritoneal dialysis system and process having a high rate of dialysate exchange providing increased dialysis efficiency through the cost effective production of large volumes of dialysate.

SUMMARY OF THE INVENTION

The above objectives are accomplished according to the invention in a peritoneal dialysis system for performing continuous peritoneal dialysis of the type which includes delivering sterile dialysate to a patient, and removing spent dialysate, by providing an automated system and process having a large, generally constant supply of unsterilized dialysate ready on demand, wherein the dialysate is sterilized in realtime as the dialysate is delivered to the patent with back-up checks on the sterilization process. A fluid circuit is connected to the dialysate supply for delivering the dialysate to the patient and delivering spent dialysate from the patient to a drain. An inflow line segment of the fluid circuit delivers the dialysate from the supply to the patient during repeated fill cycles. Advantageously, at least one in-line sterilization filter assembly is disposed in the inflow line segment for real-time sterilization of the dialysate prior to delivery of the dialysate to the patient's peritoneal cavity. An outflow line segment of the fluid circuit is provided for connection to the patient to drain spent dialysate from the peritoneal cavity during repeated drain cycles. A filter integrity test component is operatively associated with the sterilization filter assembly for conducting a realtime, in-line integrity test on the filter assembly to test for a filter failure condition which would allow contaminants into the dialysate prior to patient delivery. A test sensor in communication with the integrity testing component detects the failure condition. The sterilization filter assembly includes a main inlet port for receiving unsterilized dialysate during a dialysis mode, and receiving compressed air during a filter test phase, a sterilization filter medium through which the dialysate passes for producing sterilized dialysate, and an outlet port through which sterilized dialysate flows. The inlet and outlet ports are connected in the inflow line segment for delivery of the sterilized dialysate to the patient's peritoneal cavity. Advantageously, the filter testing component may include a source of pressurized test air, and the fluid circuit includes a test line segment connected between a pressurized air source and the inlet port acting as an air admission port of the sterilization filter assembly. An air control valve maintains the inlet port normally closed to the admission of test air, and the air control valve has an open position for delivering the test air to the filter assembly during the integrity test so that a real time integrity test of the sterilization filter assembly can be made prior to the delivery of the dialysate to the peritoneal cavity.

The test sensor may sense a drop in pressure across the filter medium, and the failure condition comprises sensing a pressure drop rate, or decay, higher than a predetermined level indicating that the filter medium is not intact. Preferably, a delivery vessel is connected to the main outlet port of the sterilization filter assembly for accumulating the sterilized dialysate prior to delivery to the patient. There is a discard line segment included in the fluid circuit connected to the delivery vessel for discarding dialysate from the delivery vessel when the failure condition is sensed. In one aspect of the invention, the control valve is set in the open position for delivering the pressurized air to the inlet port of the filter assembly after the sterilized dialysate has been delivered to the delivery vessel and prior to delivery of the dialysate to the patient. In an advantageous embodiment of the invention, a sterilization unit having a primary sterilization filter assembly and a secondary sterilization filter assembly is disposed in the fluid circuit. The secondary filter assembly has a main inlet port connected to the delivery vessel for receiving sterilized dialysate, a sterilization filter medium for sterilizing the dialysate, and an outlet port for output delivery of the dialysate. The secondary filtration assembly may also comprise secondary test control valve for admitting test air to the secondary filter assembly. Again, the dialysate inlet port may also serve as the air admission port during the filter test mode. A secondary test sensor detects a failure condition of the secondary filter assembly upon the admission of test air for testing the integrity of the secondary filter assembly. Preferably, while dialysate is held in the delivery vessel, the test control valve associated with the primary filter assembly is set in an open position to admit pressurized test air, after the dialysate has passed through the primary filter assembly; and the secondary test control valve is set in an open position for admitting pressurized test air, before passage of dialysate through the secondary filter assembly. The post and pre tests of the primary and secondary filter assemblies are preferably done at the same time. The discard line segment discards dialysate in the delivery vessel when one or more of the filter assemblies fails the integrity test. In a advantageous aspect of the invention, a pair of sterilization units may be connected in parallel in the inflow line segment wherein each one of the sterilization units in the pair includes a primary and a secondary sterilization filter assembly, and a delivery vessel. A flow control means, such as a suitable valve arrangement, passes the dialysate through a selected one of the sterilization units while isolating the other of the sterilization units from the inflow line segment. In this manner, the two units may be used in a cyclic manner, that is, one of the sterilization units may be used during a current fill cycle, while the other unit is being used to prepare and sterilize dialysate for use in the next fill cycle. In addition one unit may be used alone while the other is down for replacement or other maintenance.

A system controller controls the amount of inflow and outflow during the fill and drain cycle. Preferably, the system includes a proportioning sensor responsive to the inflow and outflow volumes for determining a volume of body waste fluid removed from the patient's peritoneal cavity during the fill and drain cycles. The system controller controls a proportioning component to adjust the osmolity of the dialysate in response to the volume of fluid, and controls the fill and drain cycles until a desired amount of waste fluid is removed from the patient.

According to the method of the invention, an automated peritoneal dialysis process includes an in-line, realtime dialysis fluid sterilization process to produce a sterilized dialysate. The sterilization process includes preparing an unsterilized dialysate effective for dialysis, passing the dialysate through at least one in-line sterilization filter assembly connected in an inflow line to the patient in realtime prior to delivery to the patient, and testing the sterilization filter assembly in realtime for a filter failure condition prior to delivering the dialysate to the peritoneal cavity of the patient. Preferably the dialysate is accumulated and held after passing the dialysate through the sterilization filter assembly, the integrity of the sterilization filter assembly is tested after passing the dialysate through the sterilization filter assembly, and the dialysate is discarded if the integrity test is failed. The process may also include providing a sterilization unit having a primary sterilization filter assembly and a second sterilization filter assembly, passing the dialysate through the primary sterilization filter assembly, accumulating the dialysate, testing the integrity of the primary and secondary sterilization filter assemblies, and passing the dialysate through the secondary sterilization filter assembly to the patient, if the tests are passed. The testing step may include testing the integrity of the primary filter assembly after passing the dialysate through the primary filter assembly, and testing the integrity of the secondary filter assembly before passing the dialysate through the secondary filter assembly. The dialysate is discarded after being accumulated if one or more of the filter assemblies fails the integrity test. In the automatic peritoneal dialysis process, dialysate is continuously delivered to the patient's peritoneal cavity, and spent dialysate is removed from the patient. The automated process comprises the steps of: (a) providing a supply of unsterilized dialysate; (b) passing the unsterilized dialysate from the supply through an in-line sterilization filter assembly to produce sterilized dialysate in realtime prior to delivery to the patient's peritoneal cavity; (c) accumulating the sterilized dialysate in a delivery vessel prior to delivery to the patient; (d) subjecting the in-line filter assembly to a filter integrity test to test for a filter failure that would allow contaminants into the dialysate prior to patient delivery; (e) delivering the sterile dialysate from the delivery vessel to the patient's peritoneal cavity after the filter integrity test is passed; and (f) repeating steps (a) through (e) until a volume of fluid has been exchanged that both achieves the desired clearance and removes a desired fluid weight from the patient. Advantageously, this can be achieved by measuring the total volume of fluid removed several times during the dialysis session by completely draining the peritoneal cavity. This can be done by automatically measuring the difference in the fill and drain amounts. The automated system then calculates the rte of removal and increases or decreases the glucose concentration accordingly.

Advantageously, the dialysis fluid is accumulated and mixed in a mixing vessel where the correct proportions of acid, bicarbonate, and glucose are measured. While the batch of dialysis fluid is being prepared in the mixing vessel, an optional pre-process integrity test may be performed on the downstream sterilization filter assembly. After a successful integrity test, the newly prepared batch of dialysis fluid is sterilized by pumping it through the sterilization filter assembly and accumulated in a delivery vessel, after which a post-process integrity test is immediately performed. In the delivery vessel, the dialysis fluid is checked for proper concentrations of acid, bicarbonate, and glucose and heated to the correct delivery temperature. Following a successful post-process integrity test on the sterilization filter assembly, the dialysis fluid is pumped from the delivery vessel through a second sterilization filter assembly, which has passed an integrity test, and then into the patient's peritoneal cavity. In another aspect, the invention includes an integrity test process that includes purging the upstream side of each sterilization filter assembly with sterile air, isolating the upstream side of the filter assemblies, allowing the pressure to stabilize, and monitoring the pressure decay for a given period of time whereby the rate of decay indicates the integrity of the filter assemblies. The patient is isolated from the integrity test by a 3-way valve upstream of the peritoneal port.

BRIEF DESCRIPTION OF THE DRAWINGS

The system and process to carry out the invention will hereinafter be described, together with other features thereof. The invention will be more readily understood from a reading of the following specification and by reference to the accompanying drawing forming a part thereof, wherein an example of the invention is shown by way of illustration and not limitation and wherein:

FIG. 9 is a symbol diagram for the various controls, sensors, and other elements of the schematic diagrams illustrating an automated peritoneal dialysis system and process according to the invention.

DETAILED DESCRIPTION OF A PREFERRED EMBODIMENT

The present invention is related to an automated peritoneal dialysis system and process such as disclosed in U.S. Pat. Nos. 4,586,920, 4,718,890, 4,747,822, 5,004,459, and 5,643,201, owned by the present inventor. In particular, these patents disclose suitable automated control systems and processes for use in performing continuous or cyclic peritoneal dialysis having application to the present invention. Accordingly, the disclosures of U.S. Pat. Nos. 4,586,920, 4,718,890, 4,747,822, 5,004,459, and 5,643,201 are incorporated into the present application by reference. Since the control systems and processes are generally known from the above incorporated patents, only so much of the control system and process necessary to the understanding of the present invention will be described.

Figure 1:
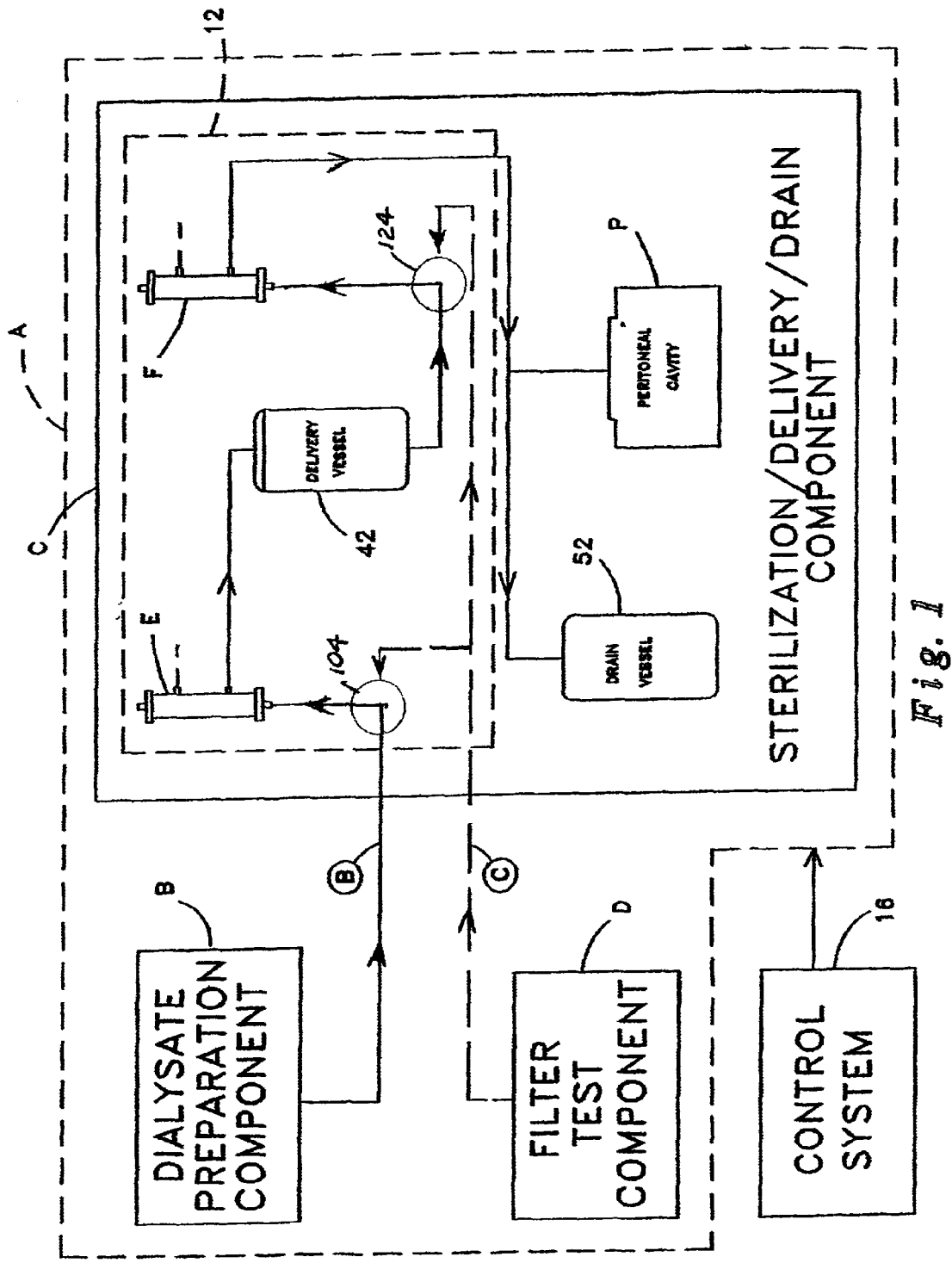
FIG. 1 is a schematic diagram of the various components of a peritoneal dialysis system and process according to the invention.

Referring to the drawings, the present invention will now be described in more detail. As can best be seen in FIG. 1, an automated peritoneal dialysis system and process, designated generally as A, is illustrated which provides a real-time uninterrupted supply of sterilized dialysis fluid upon demand in a closed system. Basically, the peritoneal dialysis system includes a dialysate preparation/ proportioning component B for mixing and proportioning water and various ingredients to provide an unsterilized osmotic dialysate, and having a system sterilization component 10 for resterilizing the system; a dialysate sterilization/ fill/drain component C having a sterilization unit 12 for realtime, in-line sterilization of the dialysate prior to patient delivery; and a filter test component D for testing the filter system prior to delivery of the dialystate to the patient. A control system 16 controls the automated dialysis system and process during repeated fill and drain cycles of dialysis fluid in and out of a patient's peritoneal cavity.

Preferably, the peritoneal dialysis system uses a process known as tidal dialysis, such as disclosed in the above incorporated patent, U.S. Pat. No. 5,643,201, to facilitate the rate of fluid exchange during repeated fill and drain cycles. Typically in such a process, a starting volume of fluid of about 2,000 cc is instilled in the patient's peritoneal cavity. About one-half of this volume is removed and replaced every few minutes. The fluid does not remain in the abdomen long enough to reach equilibrium with the body water, so there is a large concentration gradient for the toxins favoring the removal of these substances. It is to be understood, of course, that a the peritoneal dialysis system and process can also be used while continually preparing and cycling fluid through a patient's peritoneal cavity in a non-stop manner to produce a high osmotic gradient capable of rapidly exchanging toxic metabolites from the body to the dialysate. Because the fluid is being constantly exchanged, there is no dwell time in the peritoneal and the concentration gradient of the dialysate remains high to increase dialysis efficiency. The present invention can also be carried out using continuous flow peritoneal system and process, such as disclosed in incorporated patents, particularly U.S. Pat. Nos. 5,643,201, 4,718,890, and 4,586,920. In this case, the double catheter embodiments of those inventions will be used.

These techniques of continuous dialysate exchange and tidal dialysate exchange were devised to circumvent the long periods of almost no fluid flow, which are inherent in trying to remove all of the peritoneal fluid each cycle with a "batch" method. The fluid that is readily accessible to the catheter obviously flows better and faster than the fluid that is trapped in some of the secondary spaces of the peritoneal cavity. In addition, the constant increase and decrease in the fluid volume helps to promote mixing between the old and new fluid and between the main pool and the smaller pools. The dialysate is pumped into and out of the patient's peritoneal cavity, using pressure sensitive pumps. This ensures that the patient does not become overly distended. The present invention has the advantage of virtually unlimited supplies of sterilized dialysate, so that the limit on the amount of fluid it can exchange is no longer determined by economic factors. A patient has an ideal body weight based on his height and sex. Weight in excess of this ideal, or "dry" weight, is assumed to be excess fluid. According to the present invention, the dialysis system measures the total volume of fluid removed several times during the treatment session by completely draining the peritoneal cavity. The difference between the amount instilled and the amount recovered represents the amount removed from the patient. The system can then calculate the rate of fluid removal, project the amount which needs to be removed during the remaining time of the treatment and then increase, or decrease, the glucose concentration accordingly before beginning a new fill/drain cycle.

Control system 16 may include various sensors and generates various signals for controlling the exchange of dialysate. By manipulating the various control valves, pumps and switches, and monitoring the dialysis fluid with the various sensors, control system 16 effectively delivers a sterilized dialysis fluid to the peritoneal cavity of a patient in continuous or cyclic fashion which creates higher transfer gradients for the removal of toxins, which means dialysis with greater efficiency. Control system 16 is in electronic communication with various directional fluid control sensors 18 that sense the directional flow and provide signals to the control system so that the control system may direct the flow of fluid through the dialysis system. Other sensors in the dialysis system used to monitor the dialysis fluid properties and flow include fluid level sensors 20 and 22, scale 24, and temperature sensor 26 on vessel 28; fluid level sensors 30 and 32, scale 34, temperature switch 36, conductivity sensor 38, and Pt RTD sensor 40 on vessel 42; and fluid level sensors 44 and 46, scale 48, and conductivity sensor 50 on vessel 52. Preferably, the temperature sensors are thermistors operatively associated with control system 16 for monitoring the temperature of the dialysis fluid. In addition, there are pressure sensors 54, 56, 58, and 60 located at various points throughout the dialysis system which monitor the systems integrity and any possible danger to the patient of injecting an overflow of fluid. A pressure switch 62 is operatively associated with pressure sensor 60 which redirects fluid flow to a safety drain in the event of over-pressurization to prevent cavity distension.

Figure 1A:
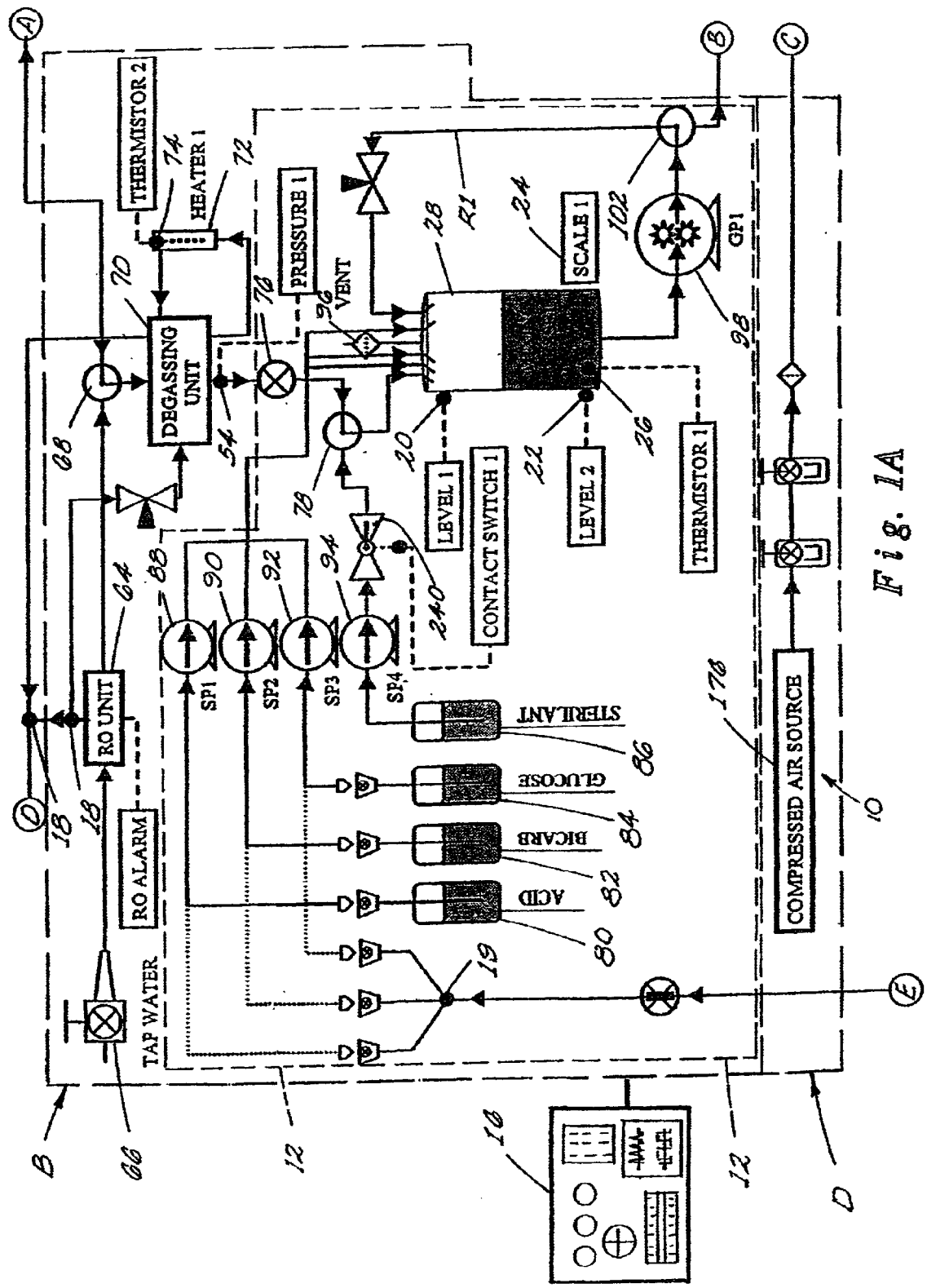
FIG. 1A is a schematic diagram of a dialysate preparation component of a peritoneal dialysis system and process according to the invention.

As can best be seen in FIG. 1A, dialysate preparation component B, includes a reverse osmosis unit ("RO unit") 64 for the purification and sterilization of normal tap water prior to combining the water with various dialysate components which make up the dialysis fluid. Reverse osmosis is a well known process in the art for passing water through a semipermeable membrane in order to remove impurities such as salt, chloramine, and bacteria from the water. Tap water from tap 66 is directed into RO unit 64 for filtration. Once the water has begun to filter, control system 16 signals three-way valve 68 to open and allow the water to collect in degassing unit 70 in order to remove any gas impurities. At this point the water is cycled through heater 72 to raise the temperature to facilitate degassing. Temperature sensor 74 monitors the temperature of the cycled water and at a specified temperature sends a signal to control system 16 which opens two-way solenoid valve 76 and three-way valve 78 to allow the heated water to enter mixing vessel 28 where it is mixed with dialysate from dialysate preparation system 12. Pressure sensor 54 is used to monitor the performance of the degassing unit 70.

Dialysate preparation component B provides a relatively constant source of unsterilized dialysis fluid to be introduced into the fluid circuit of the system. The dialysate preparation component includes various electrolyte concentrates which are diluted with the sterilized water by the proportioning component which uses proportioning pumps and weighing systems operatively associated with control system 16. In the illustrated embodiment, concentrates of acid, bicarbonates and glucose are provided in reservoirs 80, 82 and 84. System sterilization component 10 includes a sterilant 177 held in a reservoir 86 which is used to cleanse the system when needed such as between uses or after a filter failure, as will be explained more fully below. The concentrates are pumped via pumps 88, 90, and 92 to mixing vessel 28 according to signals sent from control system 16 to the pumps. Sterilant is pumped into the system through pump 94 when used. Mixing vessel 28 serves as a primary mixing vessel for the in-line production of dialysis fluid. Although the water has been purified, the mixed dialysis fluid in mixing vessel 28 is generally unsterilized insofar as use in the peritoneal cavity. It is to be understood that more than one vessel may be used to mix larger quantities of dialysis fluid. Concentrated amounts of acid 80, bicarbonate 82, and glucose 84 required for a 3 liter batch of dialysis fluid are dispensed into mixing vessel 28. The amounts may be verified gravimetrically by a load cell arrangement represented by scale 24. Degassed and heated water which has passed through RO unit 64 is run into the vessel to achieve the desired level of dilution. Dilution level is controlled using calibrated liquid level sensors in the vessel. The sensors generate signals which are received by control system 16 when the desired dilution level is reached. The components will then be mixed by using a pump to recirculate the liquid. A vent 96 is mounted on the top of mixing vessel 28 which allows air to escape as fluid levels increase. Preferably, vent 96 is a hydrophobic air filter of 0.2 um. Dialysate preparation component B prepares the unsterilized dialysate in three-liter batches, or more, and maintains a continuous supply in the delivery vessel 42.

According to the present invention, unsterilized dialysate accumulated in mixing vessel 28 is passed through sterilization/fill/drain component C, and sterilized in real-time during delivery to the patient with checks to ensure the reliability of the sterilization. In this manner, a generally constant source of large volumes of sterilized dialysis is readily available upon demand to fulfill either the continuous exchange of dialysate fluid needs or fill and drain cycles under the control of control system 16. As can best be seen in FIG. 1B, sterilization/fill/drain component C includes a realtime, in-line dialysate sterilization unit 12 (FIG. 1) which preferably includes a primary sterilization filter assembly E and a secondary sterilization filter assembly F for sterilizing the dialysate delivered from mixing vessel 28. After the appropriate mixture is determined and verified in mixing vessel 28, control system 16 operates a gear pump 98 to deliver the dialysate to a main fluid circuit, and through sterilization/fill/drain component C to the patient and then to a drain. The main fluid circuit includes flow line segments L1, L2, L3, L4, L5, and L6; recirculating line segments R1, R2, and R3; by-pass line segments B1 and B2; pressure line segment P1; and a discharge line segment D1.

Dialysis Mode

Figure 1B:
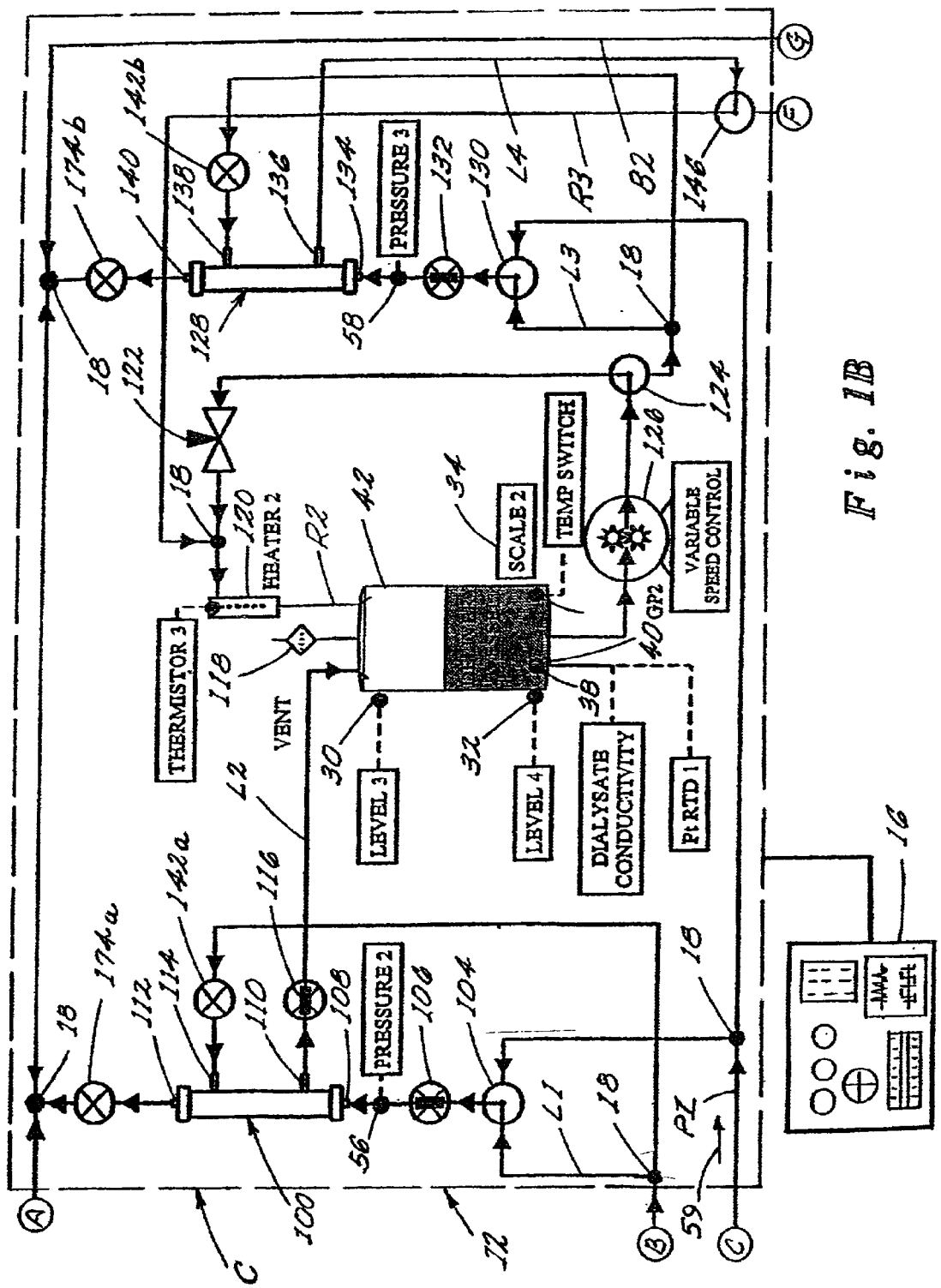
FIG. 1B is a schematic diagram of a dialysate sterilization, patient fill and drain component of a peritoneal dialysis system and process according to the invention.
Figure 8A:
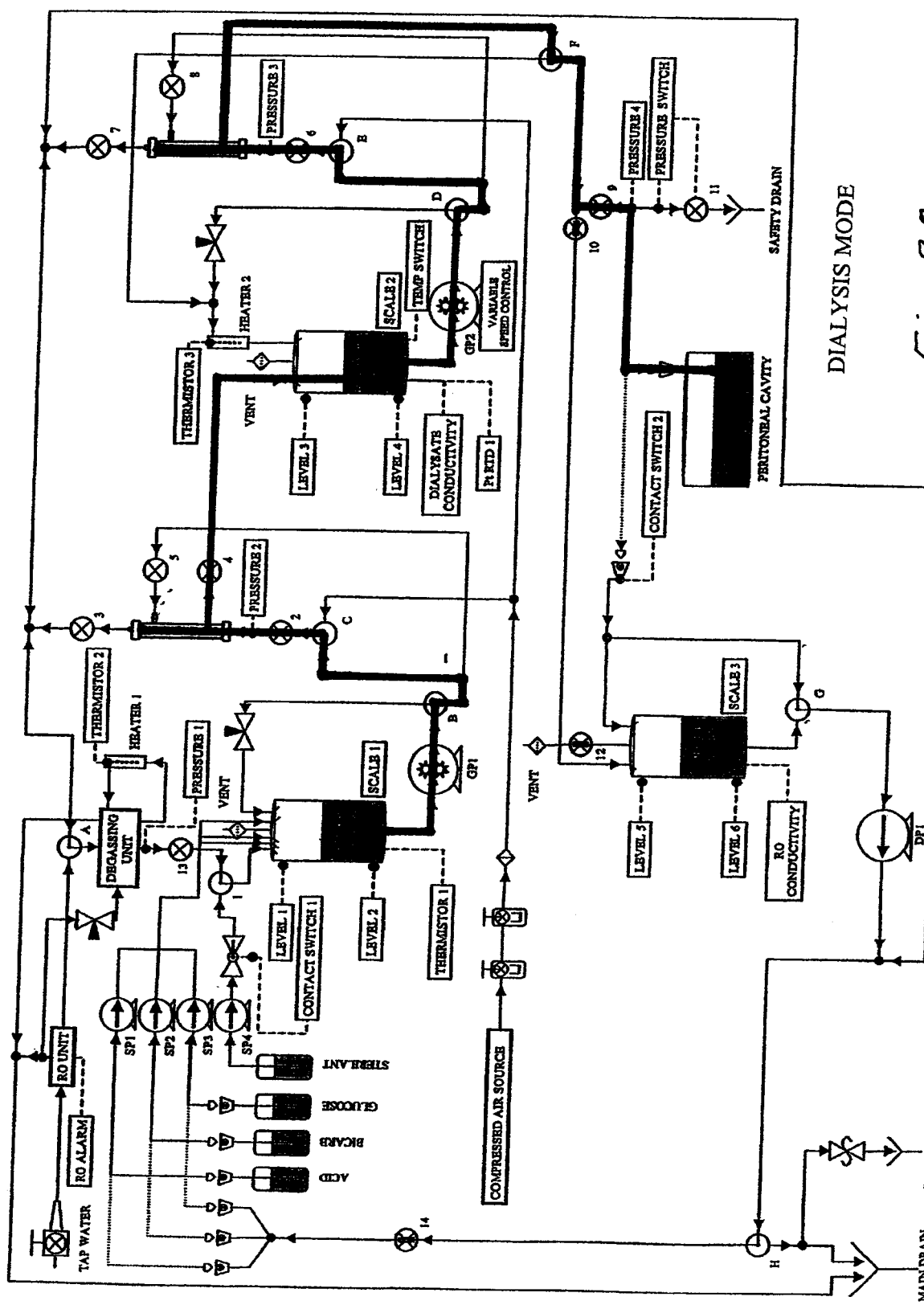
FIG. 8A is a schematic diagram of a peritoneal dialysis system and process according to the invention in a dialysis mode wherein the flow of dialysate is shown in heavy lines.

Pump 98 delivers the dialysis fluid from mixing vessel 28, thru first flow line segment L1 of the main flow circuit to primary sterilization filter assembly E and, preferably, to secondary sterilization filter assembly F, as can best be seen in FIG. 1B and the heavy lines of FIG. 8A. Line segment L1 includes gear pump 98, a three-way valve 102, a three-way, dialysate/test air control valve 104, and a two-way solenoid valve 106 connecting mixing vessel 28 to primary filter assembly E. A recirculating line segment R1 (FIG. 1A) is connected to three-way valve 102 which can be used to redirect the mixed dialysis fluid back to vessel 28 for further heating and mixing. In order for the fluid to proceed through the main fluid circuit, control system 16 controls opening of valves 102, 104, and 106 and activation of pump 98 to deliver the mixed fluid to sterilization filter assembly E. Filter assembly E includes a main inlet port 108, a main sterilized dialysate outlet port 110, and a non-sterilized dialysate outlet port 112. In addition, there is a sterilant fluid inlet port 114 for the admission of sterilant solution, as will be explained more fully hereinafter. Furthermore, in the preferred embodiment, dialysate fluid inlet port 108 also serves as a test air admission port for the admission of compressed air to test the integrity of the filter cell when three-way control valve 104 is opened to allow air from line P1 to enter the filter assembly, as described more fully below. Alternately, two separate inlet ports 114 can be provided for dialysate and test air. Outlet port 110 is connected to line segment L2 which includes a two-way solenoid valve 116. Line segment L2 runs between filter assembly E and a delivery vessel 42. Once dialysate has been sterilized in sterilization filter assembly E, it proceeds through outlet port 110 and is accumulated in delivery vessel 42 in the form of sterilized dialysate ready for use in the patient. The delivery vessel incorporates liquid level sensors 30 and 32 to gauge the amount of fluid being held. The sensors generate signals which are received by control system 16 when the desired fluid level is accumulated in vessel 42. A vent 118 is mounted on the top of vessel 42 which allows air to escape as fluid levels increase. Preferably, the vent is a hydrophobic air filter of 0.2 um. The vessel also incorporates a conductivity sensor 38 that determines the osmolality of the dialysis fluid. The mixture properties can be displayed on a display associated with control system 16, which can be used to adjust the mixture concentrations and osmolality according to the patient's needs by signaling pumps 88, 90, and 92 to add various amounts of acid, bicarbonate, and glucose (FIG. 1A). Along with the conductivity sensor, a Pt RTD sensor 40, is used to make sure that the fluid can safely be received by the patient. A flow heater 120 is connected to vessel 42 through recirculation line segment R2 which includes a three-way manual valve 122 connected to a three-way solenoid valve 124. Pump 126 cycles dialysate in delivery vessel 42 through recirculation line segment R2 and the heater until it reaches the predetermined temperature. Once the temperature is reached, a temperature switch 36 signals control system 16 that the dialysate is ready for delivery patient use. However, after passing thru primary sterilization filter assembly E, the dialysate is held in delivery vessel 42 until integrity test component D verifies that the sterilizing filter is intact, as described below.

As noted above, before the fluid enters the patient in the illustrated embodiment, the main fluid circuit preferably directs the dialysis fluid through second sterilization filter assembly F by way of line segment L3. Gear pump 126 connected to vessel 42 is used to deliver the sterilized dialysis fluid from vessel 42 to second sterilization filter assembly F by means of three-way solenoid valve 124, three-way, dialysate/air control valve 130, and a two-way solenoid valve 132. It is noted that sterilization filter assembly F has the identical inlet and outlet ports 134, 136, 138, and 140 as described above in filter assembly E for dialysate, compressed air, and sterilant. Both sterilant inlet ports 114 and 138 of filter assemblies E, F are connected to two-way solenoid valves 142a and 142b for the admission of sterilant into the sterilized fluid collection space 210 of the filter assemblies by way of sterilant line S1 and S2 during the system sterilization phase. Additionally, three-way valves 104, 130 of both assemblies are opened to admit test air from line P1 into filter assembly F to conduct an integrity test process during the dialysis phase. Pressure sensors 56 and 58 are used to monitor the integrity test as will be more fully explained below. Sterilized dialysate exiting main outlet port 136 of sterilization filter assembly F is delivered along line segment L4 to a three-way solenoid valve 146. Valve 146 is connected to a two-way solenoid valve 148 which allows delivery of dialysate to a patient's peritoneal cavity P. Alternately, recirculation line segment R3 is connected to three-way valve 146 which allows the fluid to reenter flow heater 120 for further heating, and return to delivery vessel 42. In the event that the batch of dialysis fluid does not conform to the prescribed requirements set by control system 16, a signal is sent to open drain valve 156 and direct the dialysis fluid into drain vessel 52. Pressure sensor 60 is located directly after valve 148 and monitors the pressure of fluid delivered to the peritoneal cavity to prevent over extension of the cavity. In the event fluid pressure becomes dangerous to the patient, pressure sensor 60 signals control system 16 to activate pressure switch 62 which opens safety valve 150 and drains the dialysis fluid into safety drain 152 to prevent distention of the patient's peritoneal cavity. Quick disconnect peritoneal port 154 is provided to connect a plug 155 of fluid line segment L4 to a catheter inserted in the peritoneal cavity of the patient. Quick disconnect port 158 connects flow line L5, which leads to a drain vessel 52, to peritoneal plug 155 of line L4 during the system sterilization mode. A two-way solenoid valve 156 can alternatively deliver the sterilized dialysate in line segment L4 directly to drain vessel 52 by way of drain line segment D1.

Used dialysis fluid is delivered through line segment L5 into drain vessel 52. Vessel 52 includes liquid level sensors 44 and 46 to measure the amount of fluid in vessel 52. As fluid levels rise, air escapes through vent 160 by opening two-way solenoid valve 162. Vessel 52 also incorporates a scale 48 and conductivity sensor 50 to measure the effectiveness of the used fluid. A three-way solenoid valve 164 connects the outlet of vessel 52 with a solenoid pump 166 along line segment L6 which can be used to pump the used fluid from vessel 52 to a main drain 170 or in the sterilization mode to be recycled back into the system by way of a three-way solenoid valve 168. A bypass line segment B1 is connected to three-way valve 164 which allows pump 166 to directly remove fluid from the patients peritoneal cavity catheter. Liquid level sensor 44 signals control system 16 to activate pump 166 and sends the used fluid to drain 170. A pop safety release valve is also provided at 172 that redirects drain fluid from line segment L6 to safety drain 173 as a backup precaution for main drain 170. Additionally, the non-filtered dialysis fluid which passes through the outlet ports 112 and 140 of filter assemblies E and F is directed through two-way valve 174a and 174b into bypass line segment B2 where the fluid is directed into line segment L6 and drained out of the system by main drain 170.

Figure 2:
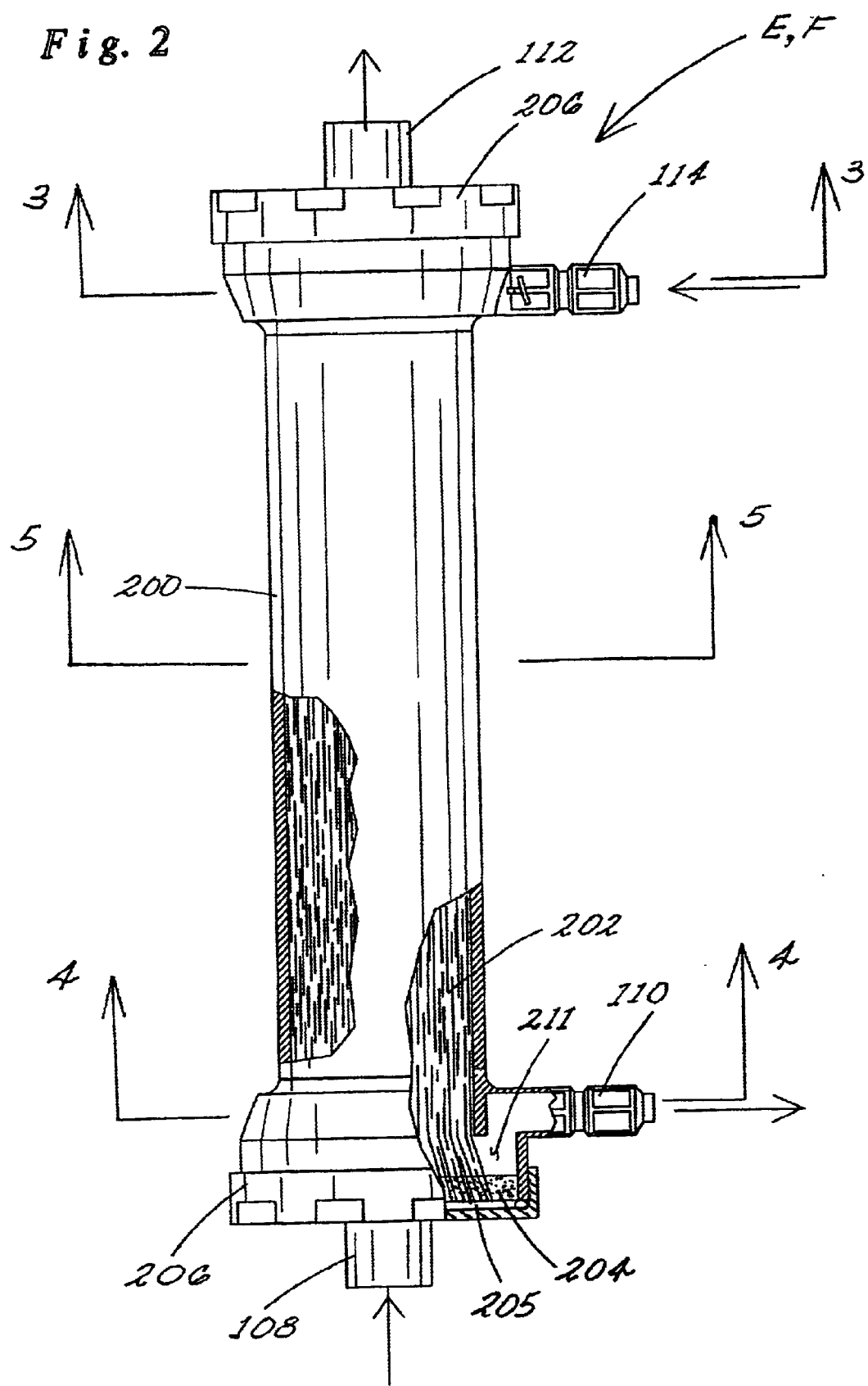
FIG. 2 is a side elevation with parts cut away of a sterilization filter assembly of a peritoneal dialysis system and process according to the invention which provides sterilization of dialysate and integrity testing of the filter in realtime during a fill cycle of the invention.
Figure 3:
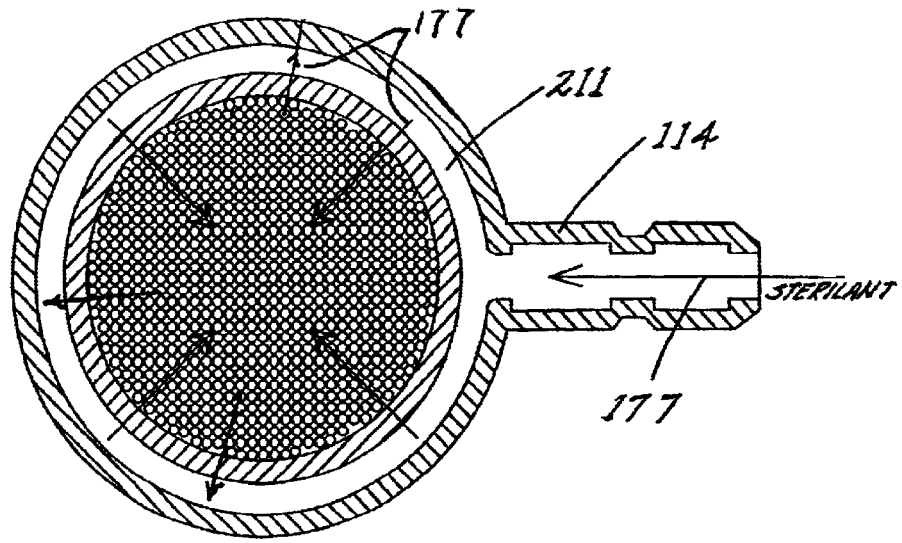
FIG. 3 is a section taken along line 3—3 of FIG. 2.
Figure 4:
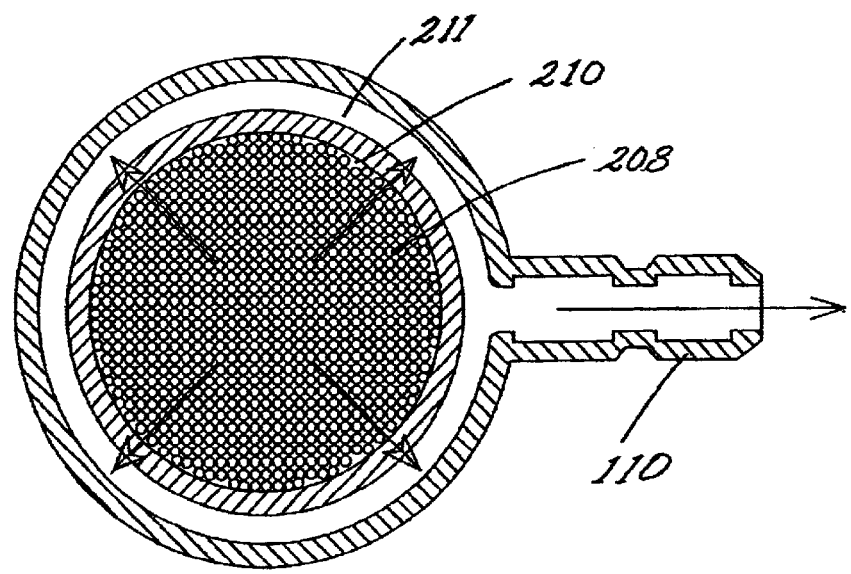
FIG. 4 is a section taken along line 4—4 of FIG. 2.
Figure 5:
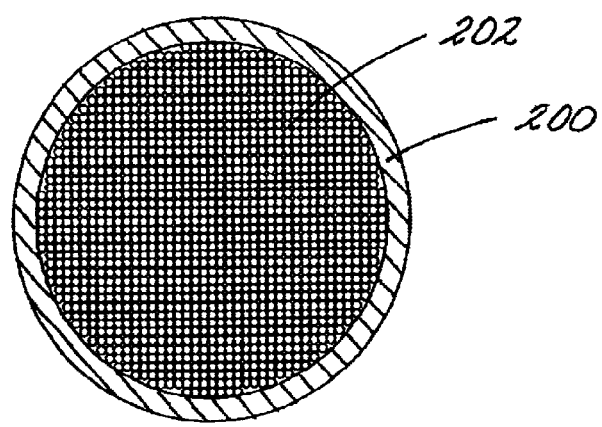
FIG. 5 is a section taken along line 5—5 of FIG. 2.

It has been found according to the present invention that suitable sterilization filter assemblies E and F can be provided by modifying filter cells used in other fields such as the hemodialysis and pharmaceutical fields. For example, a suitable filter assembly can be provided by modifying a capillary filter cell used as a hemodialyzer in a hemodialysis process available from Fresenius USA of Lexington, Mass., model F7NR, and applied according to the present invention. Since both filter assemblies are of the same construction, reference is now made to filter assembly E for an explanation herein. As can best be seen in FIGS. 2 and 3, as adapted, each sterilization filter assembly E and F may comprise a tubular housing 200 which encloses a bundle of hollow fiber tubes 202, the ends of the hollow fiber bundle being joined to the ends of the tubular housing by a molding compound 204 which seals the end of the tubular housing. The hollow-fiber bundle includes of capillary tube passages that create a semipermeable membrane for trapping bacterial and other contaminants as fluid is passed through the tubes. The dialysis fluid is filtered and sterilized as it flows radially through the semipermeable membrane material which creates the circular walls of the capillary tubes. Any contaminants larger than albumen remain trapped in the walls. The capillary tubes of the hollow-fiber bundle enclosed by the molding compound are cut at their end faces to open them in order to receive fluid. End caps 206 are placed over the ends of the tubular housing and include connection ports, which form main inlet port 108 and outlet port 112 for unsterilized dialysis fluid and compressed air. The end caps are placed on the ends of the tubular housing to seal off the ends of the sterilization filter assembly. A small gap 205 is created between the inner surface of the end cap and the molding compound providing the entrance to the capillary tubes which allows dialysis fluid to spread over the top of the molding compound inside the end caps and enter the tubes. The unfiltered dialysis fluid enters the capillary tubes through inlet port 108 provided in the end cap. Referring to FIGS. 3 and 4, a first flow space 208 is defined by the hollow interiors of fiber tubes 202 which allows the fluid to penetrate the hollow fibers in the bundle. A second flow collection space 210 is included which is defined as that space that is not occupied by the bundle of fiber tubes inside the tubular housing. Space 210 is isolated from first flow space 208 by the semipermeable membrane walls of the fiber tubes 202. Dialysis fluid is filtered by passing through the semipermeable walls of the capillary tubes, and is forced into the second flow space surrounding the tubes. The fluid is then collected in a collection space 211 at the end of the tubular housing, where it can exit the sterilization filter assembly through outlet port 110 when two-way solenoid valve 116 is opened to deliver the fluid into delivery vessel 42.Sterilant inlet port 114 is closed in this process. The molding compound, usually made of polyurethane fiber, creates a hardened disk forming a seal between the two flow spaces so that only filtered dialysis fluid can exit the sterilization filter assembly through outlet port 110. Any fluid which does not pass through the capillary tube walls remains unsterilized, and flows out the end of the hollow-fiber bundle through outlet port 112 provided in the tubular housing end cap and is delivered to main drain 170. As noted above, air is injected through main inlet port 108 to test the filter's integrity and, two-way solenoid valve 142a can be closed to prevent filtered dialysis fluid from exiting through sterilant inlet port 114. However, valve 116 and main dialysate outlet port 110 must remain open.

Sterilization Filter Test Phase

Figure 8B:
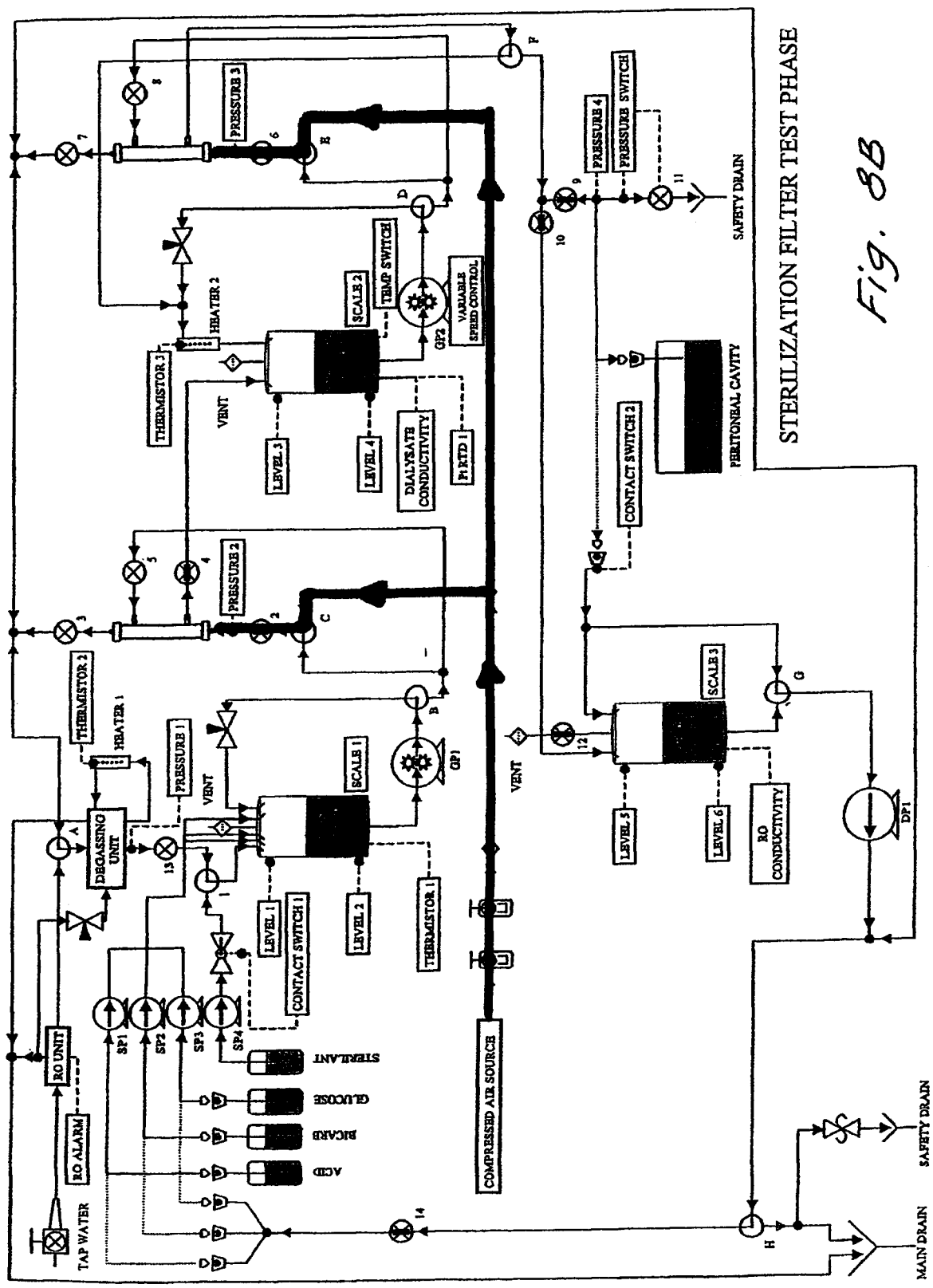
FIG. 8B is a schematic diagram of a peritoneal dialysis system and process according to the invention in a filter integrity test phase wherein the distribution of pressurized test air is shown in heavy lines.

As can best be seen in FIG. 1A, filter test component 10 is preferably provided in the form of a pressurized air test which measures the decay of a preset air pressure across the filter medium to determine if the sterilization filter is intact (FIG. 8B). In accordance with the invention, when dialysate is accumulated in mixing vessel 28, an optional pre-process integrity test may be performed on the in-line, sterilization filter assemblies E, F downstream. The dialysate is sterilized by delivering it from mixing vessel 28 through sterilization filter assembly E and into delivery vessel 42 where it is held for delivery to peritoneal cavity P. A post-process integrity test is immediately performed on sterilization filter assembly E to check for proper sterilization of the dialysate. Preferably, at the same time, a pre-process integrity test is performed on second in-line, downstream sterilization filter assembly F which follows delivery vessel 42 and precedes delivery of the dialysis fluid to a patient's peritoneal cavity. Second sterilization filter assembly F acts as a final defense against accidentally introducing any microbes or other contaminants into the patient's peritoneal cavity that might lead to a life threatening infection. Following successful post- and pre-process integrity tests on the filter assemblies, and verification of conductivity and temperature, the sterilized dialysate is pumped from delivery vessel 42 through secondary sterilization filter assembly F to the patient.

Figure 1C:
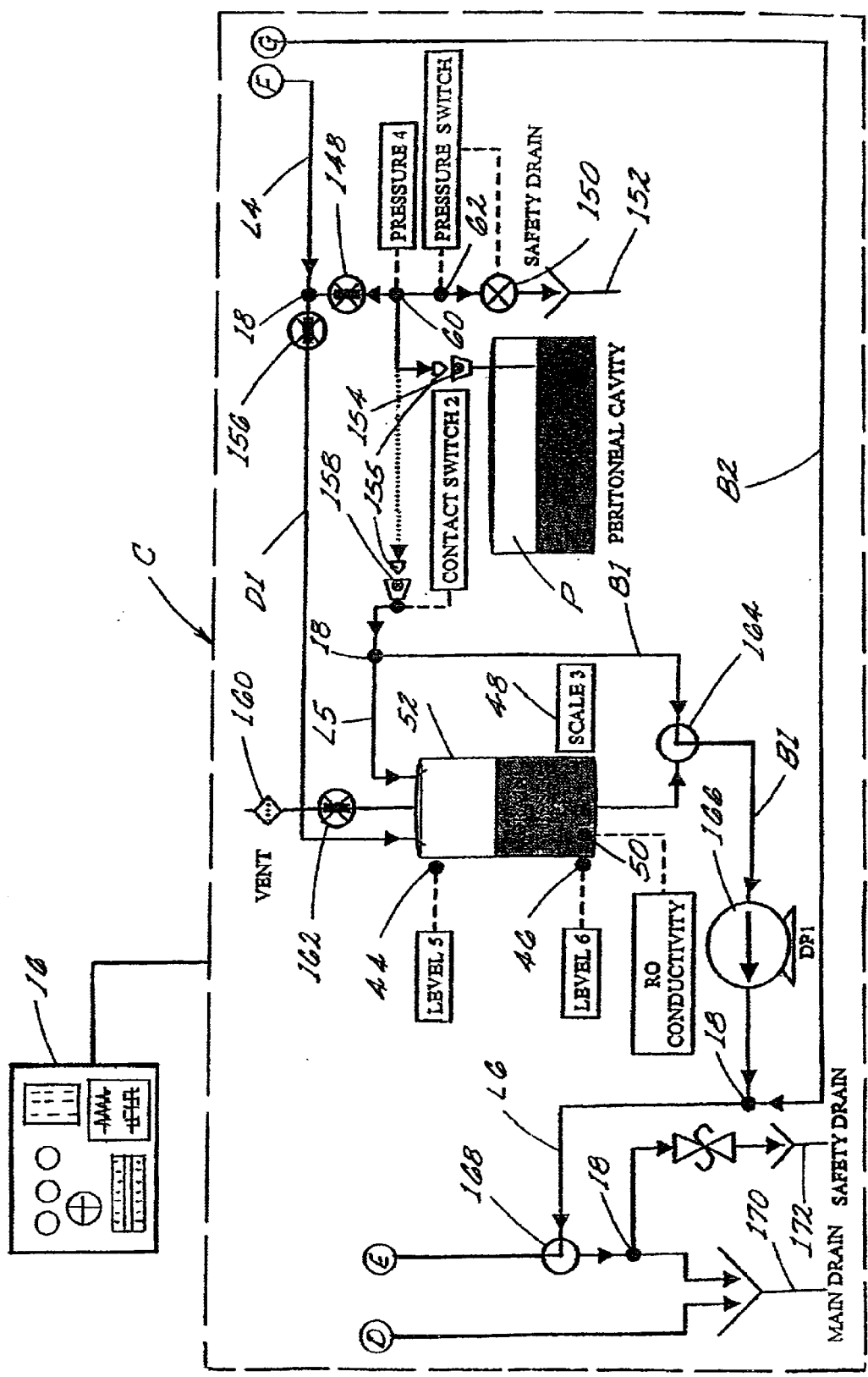
FIG. 1C is a schematic diagram of a sterilization filter test component of a peritoneal dialysis system and process according to the invention.

Since the dialysis fluid is being sterilized in real-time and in the inflow line to the patient, the integrity of the filter is of utmost importance to prevent delivery of unsterilized fluid to the patient. Accordingly, the in-line, real-time integrity test of first filter assembly E is first conducted after the fluid has left the filter assembly, but before the fluid is delivered to the patient. During this time the dialysate is held in delivery vessel 42. Preferably, the in-line test of filter assembly F is done only before passage of the dialysate, and not after. Basically, the integrity test process for filter assemblies E and F includes (1) isolating the patient from the upstream flow components which are upstream from the peritoneal port; (2) purging the upstream side of each sterilization filter assembly with sterile test air 59 from source 176; (3) applying pressurized test air to the filter assemblies; (4) allowing the pressure to stabilize; and, (5) monitoring the pressure decay for a given period of time, typically 5 minutes for the capillary filter as shown in FIG. 2. The patient is isolated from the upstream filters and other flow components by a three-way isolation valve 146. In the unlikely event flow rates or delivery pressures exceed system levels, three-way valve 146 will by-pass the flow to drain vessel 52 (FIG. 1C). Preferably, a 20 psi test pressure is applied to the filters, which is supplied by pressurized air from compressed air source 176.

Referring in more detail to FIGS. 1B and 8B, test air 59 from compressed air source 176 is directed to inlet port 108 of primary filter assembly E via three-way air control valve 104. Three-way valve 142a and two-way valve 174a are closed to allow pressure to stabilize within the filter assembly. Valves 102 and 104 are also closed to block any air flow back along line segment L1. Air pressure created by the air released from compressed air source 176 is allowed to stabilize to about 20 psi. After the pressure is reached control system 16 shuts off compressed air source 176, and monitors the pressure decay across the filter membrane of the capillary tube walls using pressure test sensor 56. The same process is used to test the integrity of sterilization filter assembly F. During the integrity test periods, the patient is isolated from upstream flow components by three-way isolation valve 146 upstream of peritoneal port connections 154 and 158 to the patient. In the unlikely event that either integrity test fails, or the conductivity measurement is unacceptable, the dialysate batch is discarded by pumping it from second vessel 42 directly into drain vessel 52 by opening a two-way, discharge control valve 156 and closing two-way valve 148. The system is then flushed with sterilant and RO water from source 86 and 64 respectively, and made ready for reuse. Depending upon the frequency of filter failures, it is a desirable characteristic of the preferred embodiment to have the system automatically switch to the other filter to replace a failed unit. If one sterilization filter assembly is down, the process may continue with the other. It is to be understood, of course, that while only a single sterilization filter assembly may be utilized with pre and post filtering integrity checks, the advantages achieved using two filter assemblies is preferred, and provides safety results not achieved by the use of a single filter assembly applied in the present invention. Once the dialysis fluid has accumulated in second vessel 42, a calibrated conductivity sensor 38 verifies the batch mixture concentrations, and the batch is stirred and precisely heated to the fluid delivery temperature desired by the patient. Following successful post-and pre-process integrity test on filter assemblies E and F, and verification of conductivity, Pt RTD, and temperature, the dialysis fluid is pumped from second vessel 42 through second filter assembly F into peritoneal cavity P through peritoneal plug 155 and port 154.

Figure 6:
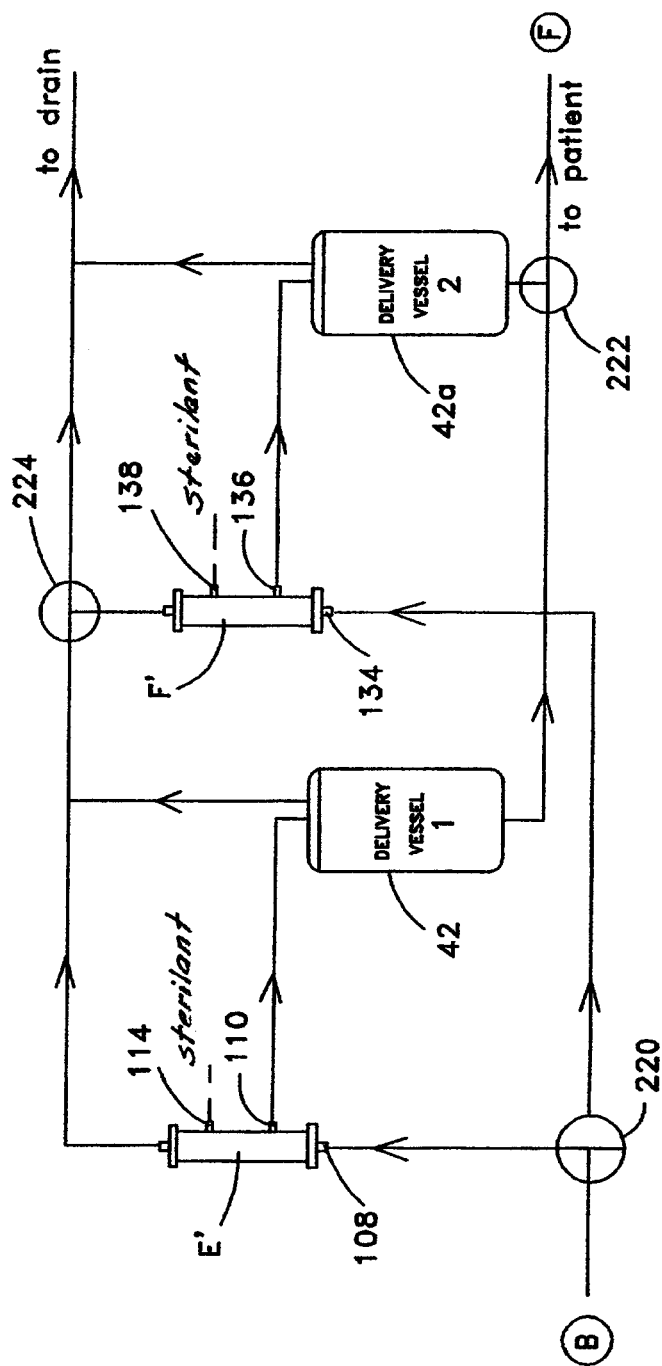
FIG. 6 is a schematic diagram of an alternate embodiment of a pair of dialysate sterilization units according to the invention.

FIG. 6 illustrates an alternate embodiment of the invention wherein two sterilization filter assemblies, E',F', are arranged to operate in parallel with each other. In this case, the sterilization filter assemblies are alternately utilized in cycles to provide a constant supply of sterilized dialysis fluid, but the dialysate does not pass in series through both assemblies. If one filter assembly needs to be removed, the system and process may continue with the other. Unsterilized dialysate is delivered to filter assembly E' by means of 3-way control valve 220. Valve 220 is controlled by control system 16 to alternately deliver the dialysate to filter assembly E' or F' in a cyclic manner. Sterilized dialysate leaves the outlet 110 of Filter assembly E' and is accumulated in delivery vessel 42. Filter assembly E' is then subjected to the integrity test while the dialysate is held in vessel 42. Once the test has passed, the dialysate is delivered from vessel 42 to the patient via 3-way valve 222. After the desired quantity of dialysate is passed thru filter assembly E' and accumulated, 3-way valve 220 diverts the next batch of unsterilized dialysate to filter assembly F'. The unsterilized dialysate passes through the filter medium and leaves filter assembly F' as sterilized dialysate thru the port 136 and is accumulated in delivery vessel 42a. Once it is determined that the filter assembly F' has passed the integrity test, 3-way valve 222 delivers the flow of sterilized dialysate 42a to the patient while blocking the flow of dialysate in delivery vessel 42. It can be seen then that the sterilization of fluid is going on in one filter assembly while sterilized dialysate from the other filter assembly is being delivered to the patient so that the filter assemblies may be cycled back and forth to deliver sterilized dialysate to the patient in a generally constant manner. If one of the filter assemblies should fail the integrity test, then the other remaining filter assembly can be utilized by itself. A third 3-way control valve 224 controls the flow of unfiltered dialysate passing through the filter assemblies to drain. While it is preferred that the system in process utilize filter assemblies in series, as described previously, the alternate embodiment may prove beneficial in some applications. Valves 220 and 222 provide a flow control arrangement for selectively cycling filters E' and F' as desired. Suitable valves for the control of test air admission to ports 108, 134 may be provided.

Figure 7:
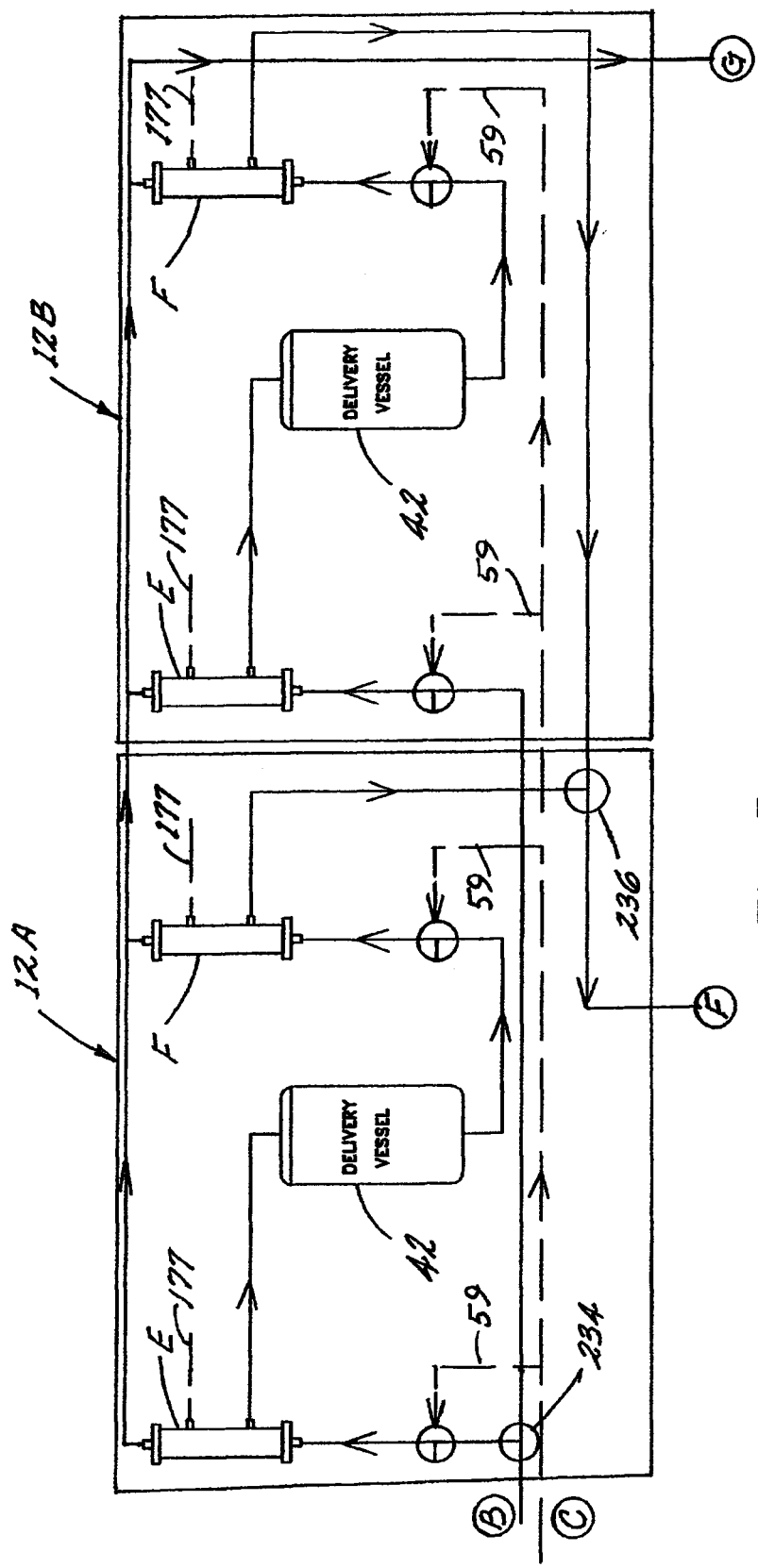
FIG. 7 is a schematic diagram of an alternative embodiment of a pair of dialysate sterilization units according to the invention.

FIG. 7 illustrates another embodiment of the invention wherein a pair of dialysate sterilization units 12 are connected in parallel in the inflow line segment of the main fluid circuit. System 12A includes a first sterilization filter assembly E, delivery vessel 42, and a second sterilization filter assembly F connected in the same arrangement shown in FIGS. 1, 1B. System 12B includes a first sterilization filter assembly E, delivery vessel 42, and a second sterilization filter assembly F connected in the same arrangement shown in FIGS. 1, 1B. In this case, either sterilization unit 12A and 12B may be operated in the peritoneal system and process while the other system is ready for use in the event there is a filter assembly failure in the operating system. For this purpose, systems 12A and 12B may be connected in the inflow line segment by flow control means composed of a 3-way valve 234, controlled by control system 16, to deliver the flow of unsterilized dialysate from preparation component B to a selected sterilization unit. Delivery vessels 42 may be selectively connected to peritoneal port 154 by 3-way valve 236 of the flow control means. Likewise, discard lines may selectively be connect to the delivery vessels using suitable control valves connected in by pass line B2 to selectively discard dialysate from either delivery vessel in the event of a filter assembly failure.

System Sterilization Mode

Figure 8C:
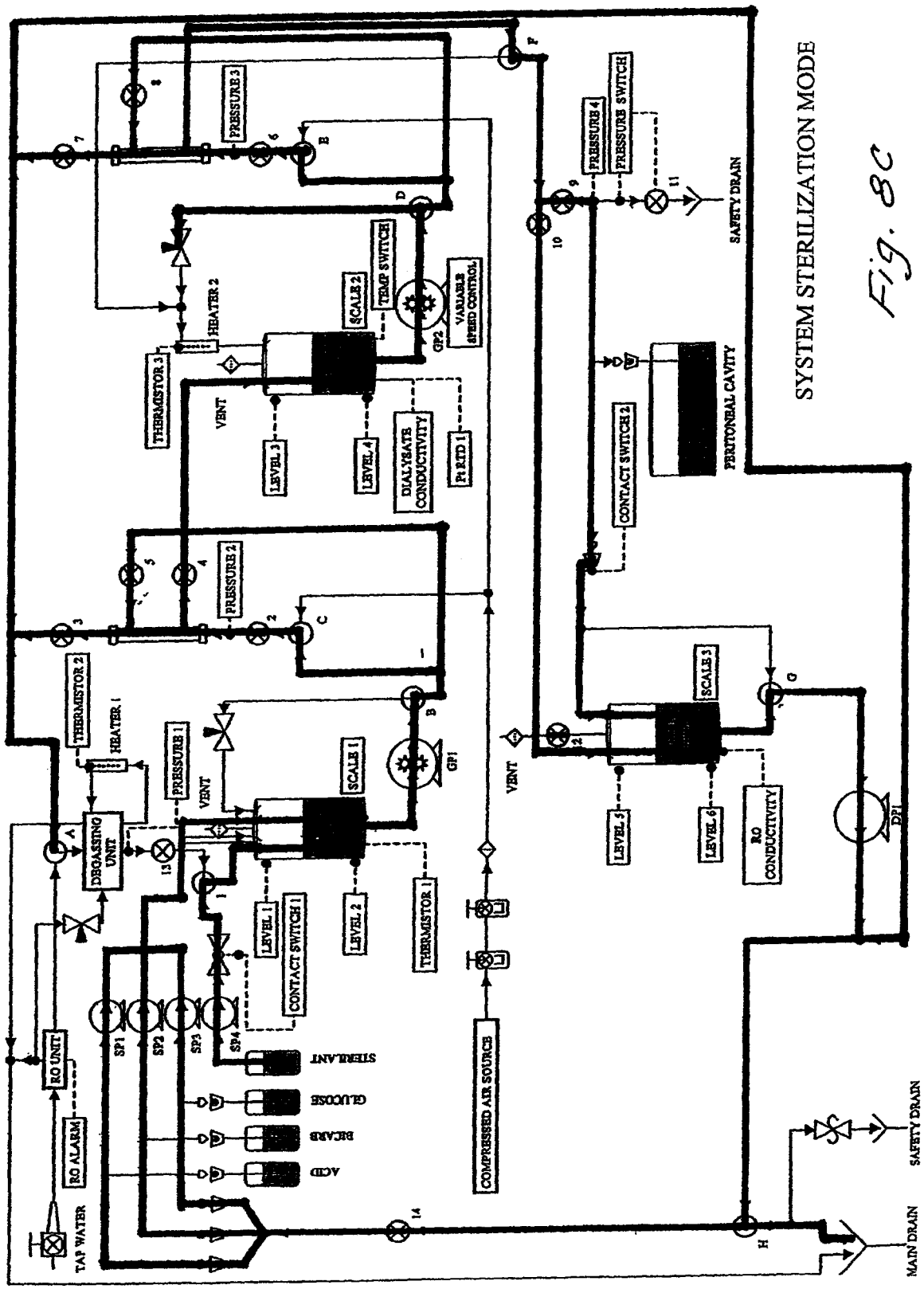
FIG. 8C is a schematic flow diagram of a peritoneal dialysis system and process according to the invention in a system sterilization mode wherein the flow of sterilant solution is shown in heavy lines.

As can best be seen in FIG. 8C, when it becomes necessary to sterilize the entire system, either due to a filter failure, or routine maintenance cleaning, filtered water from the reverse osmosis unit and a 1% Peracidin sterilant (peracetic acid and hydrogen peroxide) solution can be used to flush and resterilize the system, as shown in heavy lines in FIG. 8C. In this mode, valves 142a and 142b will open to allow opposing flow through inlet ports 114 and 138 of the filter assemblies to help dislodge any accumulated residue on the membrane surface of the capillary tubes of the hollow-fiber bundle 202 (FIGS. 1B and 3). Pump 94 is used to inject the sterilant held in container 86 into the system which is run through the various fluid circuit lines, components, and reservoirs by control system 16 controlling the various pumps and valves. The sterilization of the APDM consists of a three stage flushing and sterilant exposure process using a 1-% solution of Peracidin sterilent (peracetic acid and hydrogen peroxide) to treat all wetted components of the fluid circuit system. Following a dialysis session, the patient disconnects the peritoneal port line 155, L5 from its catheter and connects it to the recirculation port 158 of the system (dotted line flow connection in the diagrams). The patient then switches a manual 3-way diversion valve 240 to a position to allow sterilant concentrate to flow to the system (FIG. 1A). In addition to a computer-actuated 3-way valve 78 that isolates the sterilant from the initial mixing vessel, manual valve 240 provides a fail-safe against introducing sterilant to the patient in the event of a software or electrical failure. The valve handle design will physically prohibit access to the peritoneal port during sterilize mode.

The first phase of a sterilization cycle consists of a complete RO water flush of all the fluid lines and vessels to clear the system of residual dialysate (FIG. 8B). The RO water flush follows all of the same flow patterns as the dialysate. In addition, solenoid valves will open to allow opposing flow through the tangential and permeate side of the sterilization filters E, F through ports 114, 138 and 110, 136 to help dislodge any accumulated residue on the membrane surfaces. Following the RO water flush, sterilant is introduced to vessel 28. Concentrate is proportioned into the vessel and verified gravimetrically. The vessel is then filled with RO water to the appropriate dilution, verified by the liquid level sensor. Once mixed, the sterilant is then flowed throughout the system following the same flow path as the RO water flush and then allowed to dwell. In order to minimize the amount of sterilant required to expose all surfaces, especially in the 3L vessels, a single 3L dilution of sterilant can be flowed through the system in a batch mode. This is achieved by allowing the sterilant to dwell in a particular vessel for a given period of time, and then pumping the sterilant to the next vessel. During long periods storage of the system, the sterilant batch can be recycled throughout the system, rather than pumping it to drain. The third phase of the sterilization process occurs just prior to initializing a dialysate session. This phase is identical to the first RO water flush and is used to fully purge the system of residual sterilant. In order to ensure all sterilant has been flushed, a conductivity measurement will be taken of the RO water in vessel 42.

Thus, it can be seen that an advantageous construction can be had for an automated peritoneal dialysis system and process according to the invention wherein an unsterilized dialysate provided by a preparation and portioning system component is sterilized after it leaves the preparation component by passing the dialysate thru one or more in-line sterilization filter assemblies to provide large volumes of dialysate for exchange. The key to the realtime sterilization system and process is the protection that the sterilization membrane must remain intact. Advantageously, the integrity of the sterilization medium or membrane is established during the process before patient delivery by passing the dialysate thru the sterilizing membrane into a sterile holding vessel. The integrity of the membrane is then tested with air pressure. Two sterilization assemblies may be used and selectively connected in a series or a by-pass connection. In the event that one sterization assembly should fail during a treatment session, the system can simply shut down that flow line segment and operate the flow line segment of the other sterilization assembly. The failed assembly can then be replaced. The main reason to use sterilization assemblies to the point of failure would be the convenience of not having to replace them. In practice, the sterilization assemblies will likely be replaced on a regular basis; probably every three months depending upon experience.

While a preferred embodiment of the invention has been described using specific terms, such description is for illustrative purposes only, and it is to be understood that changes and variations may be made without departing from the spirit and scope of the claims below. Other embodiments and modifications may become apparent to those skilled in the art upon reading the foregoing specification, but such modifications and embodiments may be within the scope of the invention which is limited only by the claims below.

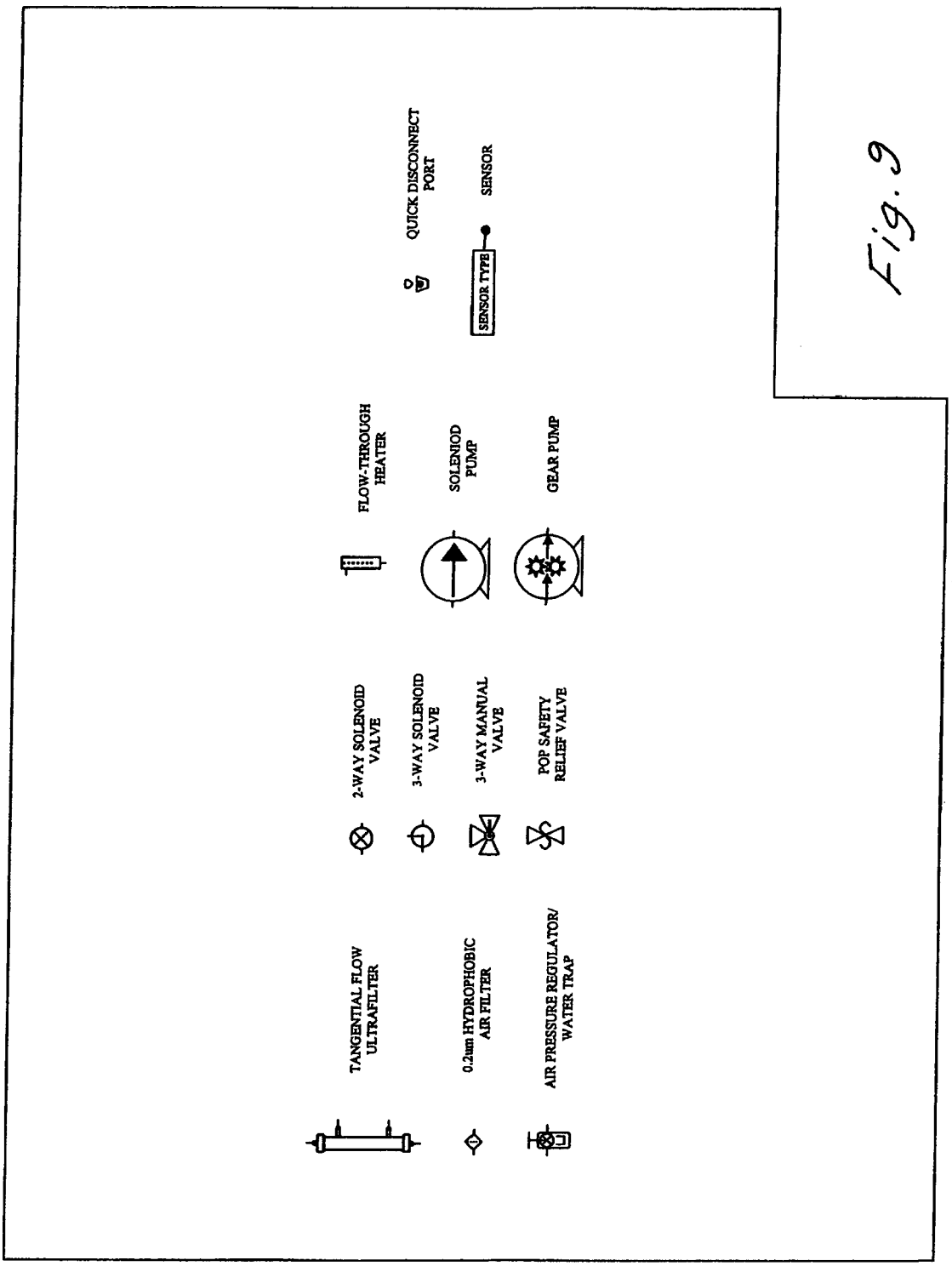

What is claimed:

1. An automated peritoneal dialysis system for performing continuous peritoneal dialysis of the type which includes repeated cycles of delivering sterile dialysate to a patient's peritoneal cavity and removing spent dialysate from the patient's cavity wherein said system comprises:
    a dialysate preparation component providing a generally continuous supply of proportioned osmotic dialysate ready on demand which is effective for dialysis;
    a fluid circuit connected to said dialysate supply for delivering a flow of the dialysate to the patient and a flow of spent dialysate from the patient to a drain;
    an inflow line segment in said fluid circuit for delivering said dialysate from said supply to the patient;
    a dialysate sterilization component having an in-line sterilization filter assembly disposed in said inflow line segment for real-time sterilization of said dialysate in said flow line segment prior to delivery of the dialysate to the patient's peritoneal cavity during the peritoneal dialysis;
    an outflow line segment included in said fluid circuit for connection to the patient to drain spent dialysate from the peritoneal cavity;
    a filter integrity test component operatively associated with said sterilization filter assembly for conducting a realtime, in-line integrity test on said filter assembly during peritoneal dialysis and prior to patient delivery to test for a filter failure which would allow contaminants into said dialysate;
    a control system controlling the filling and draining of the patient's peritoneal cavity to exchange a volume of dialysate until a desired fluid weight has been removed from the patient;
    a system sterilization component associated with said fluid circuit for sterilizing said fluid circuit including said dialysate sterilization component after a filter failure; and
    said control system controlling said filter test component and said system sterilization component aperative to test said sterilization filter assembly and sterilize the fluid circuit in the event of a filter failure.

2. The system of claim 1 including a proportioning component for adjusting the osmolality of said dialysate supply; and a proportioning sensor for determining the amount of fluid waste removed from the patient's peritoneal cavity during dialysis; and said control system controlling said proportioning component in response to said amount of removed fluid waste to adjust the osmoality of the dialysate as needed until a desired amount of waste is removed from the patient.

3. The system of claim 1 wherein said sterilization filter assembly includes an main inlet port for receiving unsterilized dialysate, a sterilization filter medium through which said dialysate passes for producing sterilized dialysate, a main outlet port through which sterilized dialysate flows; and said main inlet and outlet ports being connected in said inflow line segment for delivery of said sterilized dialysate to the patient's peritoneal cavity.

4. The system of claim 3 wherein said filter testing component includes a source of pressurized test air to said sterilization filter assembly, a test air control valve having a normally closed position during dialysate flow, and said air control valve having an open position for delivering said test air to said filter assembly during said integrity test so that a real time integrity test of said sterilization filter assembly can be made prior to delivering of said dialysate into the peritoneal cavity.

5. The system of claim 4 wherein said main inlet port serves as an air admission port during said filter test, and said air control valve is arranged in said fluid circuit to selectively deliver dialysate and test air to said inlet port and filter medium.

6. The system of claim 4 including a pressure sensor in communication with said filter assembly for sensing said filter failure.

7. The system of claim 4 including a delivery vessel connected to said main outlet port of said sterilization filter assembly for accumulating said sterilized dialysate during the integrity test and prior to delivery to said patient.

8. The system of claim 7 including a discard line segment included in said fluid circuit connected to said delivery vessel for discarding dialysate from said delivery vessel when said filter failure is sensed.

9. The system of claim 7 wherein said air control valve is set in said open position for delivering said pressurized air to said filter assembly after said sterilized dialysate has been delivered to said delivery vessel and prior to delivery of said dialysate to the patient.

10. The system of claim 7 wherein said sterilization filter assembly constitutes a primary sterilization filter assembly; and including a secondary sterilization filter assembly disposed in said fluid circuit, said secondary filter assembly having a main inlet port connected to said delivery vessel for receiving sterilized dialysate, a sterilization filter medium for sterilizing said dialysate, and a main outlet port for output delivery of said dialysate.

11. The system of claim 10 wherein said secondary filtration assembly is connected to said source of pressurized test air, and including a secondary test air control valve for admitting test air to the secondary filter assembly, and a secondary test sensor for detecting a failure condition of the secondary filter assembly upon the admission of test air to the secondary filter assembly for testing the integrity of the secondary filter assembly.

12. The system of claim 11 wherein said test control valve associated with said primary filter assembly is set in an open position to admit pressurized test air after said dialysate has passed through said primary filter assembly, and said secondary test control valve is set in an open position for admitting pressurized test air before passage of dialysate through said secondary filter assembly.

13. The system of claim 12 including a discard line segment in said fluid circuit for discarding dialysate passed through one or more of said filter assemblies when one or more of said filter fails said integrity test.

14. The system of claim 3 wherein said sterilization filter assembly includes a fluid outlet for delivery of unsterilized dialysate.

15. The system of claim 1 including a sterilization unit wherein said sterilization filter assembly is a primary filter assembly of said sterilization unit, and said sterilization unit includes a secondary sterilization filter assembly disposed in said fluid circuit, said secondary filter assembly having a main inlet port for receiving sterilized dialysate which has passed through said primary filter assembly, a sterilization filter medium for sterilizing said dialysate, and a main outlet port for delivering dialysate to the patient's peritoneal cavity.

16. The system of claim 15 wherein said primary and secondary filtration assemblies are connected to a source of pressurized test air, and including primary and secondary test control valves for admitting pressurized air to the second filter assembly during said filter test while blocking off said air during flow of dialysate; and primary and secondary test sensors for detecting a filter failure of the primary and secondary filter assemblies upon the admission of pressurized air to said primary and secondary filter assemblies for testing the integrity of the filter assemblies prior to delivery of said dialysis fluid to the patient.

17. The system of claim 16 wherein said primary and secondary test control valves are set in an open position for admitting test air after said dialysate has passed through said primary filter assembly but before said dialysate is passed through said secondary filter assembly.

18. The system of claim 17 including a delivery vessel connected to said main outlet port of said primary filter assembly for holding said dialysate passed through said primary filter assembly during said integrity tests; and said delivery vessel being connected to said main inlet port of said secondary filter assembly for delivering said dialysate through said secondary filter assembly and to the patient after said integrity tests are passed.

19. The system of claim 18 including at least one discard line segment for discarding dialysate passed through said filter assemblies when either filter medium fails said integrity test.

20. The system of claim 15 including a first sterilization unit and a second sterilization unit connected in parallel in said inflow line, and valve control means for selectively delivering unsterilized dialysate through said second sterilization unit while sterilized dialysate from said first sterilization unit is delivered to said patient.

21. The system of claim 1 wherein said system sterilization component includes a automated sterilant control valve for admitting a sterilant solution to said main fluid circuit including said sterilization filter assembly to flush and resterilize the fluid circuit after a filter failure and replacement.

22. The system of claim 21 including a manual sterilant control valve preventing flow of said sterilant during dialysis, said manual control valve having an open position sterilant to flow to proportioning component to proportion said sterilant with sterile water for sterilizing said main circuit after completion of dialysis.

23. The system of claim 1 wherein said control system controls said filter integrity test component to test said sterilization filter assembly after said dialysate has passed through said filter assembly and before said dialysate is delivered to the patient during the peritoneal dialysis.

24. The system of claim 23 including a delivery vessel for accumulating said dialysate while said filter assembly is being tested.

25. An automated peritoneal dialysis system for performing continuous peritoneal dialysis of the type which includes a fluid circuit for delivering sterile dialysate to the peritoneal cavity of a patient and removing spent dialysate from the patient; and a system controller for controlling the flow of dialysate during said fill and drain of dialysate wherein said system comprises:

a generally continuous supply of unsterilized dialysate for supplying large volumes of dialysate on demand;

an inflow line segment included in said fluid circuit for delivering dialysate from said supply to the patient;

an outflow line segment included in said fluid circuit for connection to the patient's peritoneal cavity to drain spent dialysate from the peritoneal cavity;

an in-line sterilization filter assembly disposed in said inflow line segment for realtime sterilization of said unsterilized dialysate during flow of said dialysate in said inflow line segment and prior to patient delivery;

said sterilization filter assembly including an inlet port connected in said inflow line segment for receiving unsterilized dialysate, a sterilization filter medium through which said dialysate passes for producing sterilized dialysate, and an outlet port connected in said inflow line segment through which sterilized dialysate flows for delivery to the patient during the peritoneal dialysis;

a filter test component operatively associated with said sterilization filter assembly for conducting a realtime integrity test on said filter assembly to test for a filter failure condition which would allow contaminants into said dialysate prior to patient delivery, wherein said system controller is operative to control said filter test component to test said sterilization filter assembly after said dialysate has passed through said filter assembly and before said dialysate is delivered to the patient during the peritoneal dialysis; and a test sensor in communication with said testing component for detecting said failure condition;

whereby large volumes of sterilized dialysate are available on demand in realtime during the peritoneal dialysis process to provide a high rate of dialysate exchange during repeated dialysate fill and drain cycles until a desired weight of fluid waste is removed from the patient.

26. The system of claim 25 wherein said test component includes a source of pressurized test air connected to said sterilization filter assembly, a test air control valve preventing admission of test air during dialysis, and said air control valve having an open position for delivering said test air to said filter assembly during said integrity test so that a filter integrity test of said sterilization filter assembly can be made in realtime prior to the injection of said dialysate into the peritoneal cavity.

27. The system of claim 26 wherein said air control valve is set in said open position for delivering said pressurized air to said filter assembly during said integrity test after said sterilized dialysate has passed through said sterilization filter assembly and prior to delivery of said dialysate to the patient.

28. The system of claim 26 wherein said test sensor includes a pressure sensor in communication with said filter assembly for sensing a filter failure condition.

29. The system of claim 25 wherein sterilization filter assembly includes a fluid outlet for delivery of unsterilized dialysate.

30. The system of claim 25 wherein said fluid circuit includes a discard line segment for discarding dialysate passed through said filter assembly in the event said filter medium fails said integrity test.

31. The system of claim 30 including a delivery vessel connected to said outlet port of said sterilization filter assembly for accumulating said sterilized dialysate during the filter integrity test and prior to delivery to said patient, and said discard line segment being connected to said delivery vessel.

32. The system of claim 25 wherein said dialysate is supplied for repeated drain and fill cycles, said sterilization filter assembly constitutes a first sterilization filter assembly; and including a second sterilization filter assembly connected in parallel to said first sterilization filter assembly, and a flow control arrangement for passing unsterilized dialysate thru said first and second sterilization filter assemblies in a cyclic manner so that sterilized dialysate from said first sterilization filter assembly is used during a present fill cycle and sterilized dialysate from said second sterilization filter assembly is used during a next fill cycle.

33. The system of claim 32 wherein said flow control arrangement selectively isolates one of said first and second sterilization filter assemblies from the other so that only one of said first and second filter assemblies is used during repeated fill cycles.

34. The system of claim 25 a delivery vessel for accumulating said dialysate after passing through said sterilization filter assembly and during testing of said filter assembly prior to delivery of said dialysate to the patient.

35. An automated peritoneal dialysis system for performing continuous peritoneal dialysis of the type which includes a fluid circuit for delivering sterile dialysate to a patient's peritoneal cavity and removing used dialysate from the patient; and a system controller for controlling said filling and draining to achieve an effective dialysis, wherein said system comprises:
 a steady supply of a large volume dialysate effective for dialysis available on demand;
 an inflow line segment included in said fluid circuit for connection to the patient to deliver dialysate from said supply;
 an outflow line segment included in said fluid circuit for connection to the patient to drain spent dialysate from the peritoneal cavity;
 a sterilization unit included in said inflow line segment which includes:
  a primary in-line sterilization filter assembly disposed in said inflow line segment for real-time sterilization of said dialysate during flow of said dialysate in said inflow line segment prior to patient delivery;
  a secondary in-line sterilization filter assembly disposed in said inflow line segment for real-time sterilization of said dialysate during flow of said dialysate in said inflow line segment prior to patient delivery;
 said primary sterilization filter assembly unit including an inlet port connected in said inflow line segment for receiving said dialysate from said supply, a sterilization filter medium through which said dialysate passes for producing sterilized dialysate, and an outlet port connected in said inflow line segment through which sterilized dialysate flows;
 a delivery vessel included in said inflow line connected to said outlet port of said primary sterilization filter assembly for accumulating said dialysate;
 said secondary filter assembly having an inlet port connected to said delivery vessel for receiving said accumulated dialysate, a sterilization filter medium for sterilizing said dialysate, and an outlet port for delivering dialysate to the patient; and
 a filter test component operatively associated with said primary and secondary sterilization filter assemblies for conducting a real-time integrity test on said filter assemblies to test for a filter failure condition which would allow contaminants into said dialysate while said dialysate is accumulated and prior to patient delivery;
  whereby filling and draining of the peritoneal cavity with dialysate may be repeated by the system controller as needed using a realtime supply of sterilized dialysate ready on demand providing a high rate of dialysate exchange.

36. The system of claim 35 wherein said fluid circuit includes at least one discard line segment for discarding dialysate passed through said primary and secondary filter assemblies in the event one of said first and second filter mediums fails said filter failure condition.

37. The system of claim 36 wherein said discard line segment is connected to said delivery vessel.

38. The system of claim 35 said primary and secondary filter assemblies are connected to a source of pressurized air, and including primary and secondary test control valves for selectively admitting pressurized air to the primary and secondary filter assemblies, and including primary and secondary test sensors for detecting said failure condition of the primary and secondary filter assemblies upon the admission of pressurized air to said primary and secondary filter assemblies for testing the integrity of the filter assemblies prior to delivery of said dialysis fluid to the patent.

39. The system of claim 38 wherein said primary and secondary test control valves are set in said open position for delivering said pressurized air to said filter assemblies during said integrity test after said sterilized dialysate has been delivered to said delivery vessel and prior to delivery of said dialysate to the patient.

40. The system of claim 38 wherein said test control valves are set in said open position before said dialysate is passed through said secondary filter assembly.

41. The system of claim 35 including a pair of said sterilization units connected in parallel in said inflow line segment wherein each one of sterilization units includes said primary and secondary sterilization filter assemblies, and said delivery vessel; and including flow control means for passing said dialysate thru a selected one of said sterilization units while isolating said other of said sterilization units from said inflow line segment.

42. An automated peritoneal dialysis process for performing continuous peritoneal dialysis of the type which includes providing a supply of sterile dialysate to fill the patient's peritoneal cavity and removing spent dialysate from the patient's cavity, said process comprising the steps of:
 (a) providing a generally continuous supply of large volumes of unsterilized dialysate;
 (b) passing said unsterilized dialysate from said supply through an in-line sterilization filter assembly to produce sterilized dialysate in realtime during the process prior to delivery to the patient's peritoneal cavity;
 (c) accumulating said sterilized dialysate in a delivery vessel prior to delivery to the patient;
 (d) subjecting said in-line filter assembly to a realtime filter integrity test during the process to test for a filter failure that would allow contaminants into said dialysate prior to patient delivery;

(e) delivering said sterile dialysate from said delivery vessel to the patient's peritoneal cavity after said filter integrity test is passed; and (f) repeating steps (a) through (e) until a desired volume of dialysate is exchanged.

43. The process of claim 42 including discarding said dialysate from said delivery vessel in the event said filter integrity test is not passed.

44. The process of claim 42 wherein said filter assembly is subjected to said filter integrity test after said dialysate is passed through said filter assembly and before delivery of said dialysate to the patient.

45. The process of claim 42 wherein said sterilization filter assembly constitutes a first filter assembly, and including providing a second sterilization filter assembly through which dialysate may be passed for sterilization.

46. The process of claim 45 including providing said first and second sterilization filter assemblies connected in parallel so that said dialysate may be selectively passed through either filter assembly while isolating said other filter assembly.

47. The process of claim 45 wherein said process includes accumulating said dialysate which has been passed through said primary sterilization filter assembly in said delivery vessel, and delivering said dialysate from the delivery vessel through said secondary sterilization filter assembly to sterilize said dialysate in real-time prior to entering the patient's peritoneal cavity.

48. The process of claim 47 including testing said primary and secondary filter assemblies for filter failure which would allow contaminants into said dialysate after said dialysate is passed through said primary filter assembly and before said dialysate is passed through said secondary filter assembly prior to patient delivery.

49. The process of claim 48 including delivering said sterile dialysate from the delivery vessel through said secondary sterilization filter assembly to the peritoneal cavity of a patient after the filter failure test is passed, and discarding said dialysate from the delivery vessel in the event the filter failure test is not passed.

50. The process of claim 47 including:
   determining the amount of said sterile dialysate delivered into the peritoneal cavity of a patient;
   generating a first signal determined from the amount of said sterile dialysate delivered to the peritoneal cavity of a patient;
   draining spent dialysate from the patient's peritoneal cavity
   determining the amount of spent dialysate drained from the peritoneal cavity of a patient;
   generating a second signal determined from the amount of spent dialysate drained from the peritoneal cavity of a patient;
   controlling the delivery of said sterile dialysate to the peritoneal cavity of a patient in response to said first and second signals until a desired volume of body fluid is removed from the peritoneal cavity of a patient.

51. The process of claim 50, wherein said process further comprises the step of calculating the amount of the body fluid waste removed from the patient after totally draining said dialysate for proportioning an amount of osmotic substance in said dialysate for subsequent fill and drain cycles.

52. In a continuous, cyclic peritoneal dialysis process, an in-line, realtime dialysis fluid sterilization process to produce a sterilized dialysate comprising:

preparing an unsterilized osmotic dialysate effective for dialysis;

passing said dialysate through at least one in-line sterilization filter assembly connected in an inflow line to the patient in realtime during the process prior to delivery to the patient; and testing said sterilization filter assembly in realtime during the process after said passing step for a filter failure condition prior to delivering said dialysate to the peritoneal cavity of the patient.

53. The process of claim 52 including accumulating the dialysate after passing the dialysate through said sterilization filter assembly, testing the integrity of said sterilization filter assembly while the dialysate is accumulated and discarding the accumulated dialysate if the integrity test is failed.

54. The process of claim 52 including providing a sterilization unit having a primary sterilization filter assembly and a secondary sterilization filter assembly, passing said dialysate through said primary sterilization filter assembly, accumulating said dialysate, testing the integrity of said primary sterilization filter assembly, before passing said dialysate through said secondary sterilization filter assembly.

55. The process of claim 54 including testing the integrity of said secondary filter assembly before passing said dialysate through said secondary filter assembly.

56. The process of claim 55 including discarding said dialysate after being accumulated if one or more of said filter assemblies fails said integrity test.

57. The process of claim 54 including providing a pair of said sterilization units connected in parallel in said inflow line segment wherein each one of the sterilization units includes a primary and a secondary sterilization filter assembly, and a delivery vessel.

58. The process of claim 57 including passing the dialysate through a selected one of the sterilization units while isolating the other sterilization unit from the inflow line segment.

59. The process of claim 57 including selecting one of said sterilization units for the passage of dialysate in a cyclic manner so that one of the sterilization units is used during a current fill cycle, while the other unit is used to prepare and sterilize another batch of dialysate for use in the next fill cycle.

60. The process of claim 52 wherein testing of said sterilization filter assembly includes the steps of:
   providing a source of sterile pressurized air for connection to said in-line sterilization filter assembly;
   purging an upstream side of said filter assembly upstream of said peritoneal cavity with sterile pressurized air;
   isolating said filter assembly upstream of said peritoneal cavity allowing the pressure to stabilize; and
   monitoring the pressure decay for a given period of time.

61. The process of claim 52 including providing first and second filter assemblies in parallel flow arrangement in said fluid circuit; and passing dialysate thru said first filter assembly and accumulating said dialysate in a first delivery vessel, subjecting said first filter assembly to an integrity test, and delivering said dialysate to said patient if the test is passed in a current fill cycle; and passing dialysate thru said second filter assembly and accumulating said dialysate in a second delivery vessel, subjecting said first second assembly to an integrity test, and delivering said dialysate from said second delivery vessel to said patient if the test is passed during a next fill cycle.

62. The process of claim 52 comprising the steps of:

carrying out said automated peritoneal dialysis process using an automatic peritoneal dialysis machine having a fluid circuit;

providing a sterilant solution to sterilize said peritoneal dialysis machine;

providing sterile water to sterilize said peritoneal dialysis machine;

flushing said continuous peritoneal dialysis machine with said sterilant solution; and flushing said peritoneal dialysis machine with said sterile water.

63. The process of claim 62 including pressurizing said sterilant solution to force opposing flow of said sterilant through said in-line sterilization filter assembly to dislodge accumulated residue on the filter medium.

64. The process of claim 62 including pressurizing said sterile water to force opposing flow of said water through said in-line sterilization filter assembly to dislodge accumulated residue on the filter surface membrane.

* * * * *

UNITED STATES PATENT AND TRADEMARK OFFICE
CERTIFICATE OF CORRECTION

PATENT NO.         : 6,758,975 B2                                                                Page 1 of 8
APPLICATION NO.    : 10/075175
DATED              : July 6, 2004
INVENTOR(S)        : Alan M. Peabody et al.

It is certified that error appears in the above-identified patent and that said Letters Patent is hereby corrected as shown below:

Delete title page showing an illustrative figure and substitute the attached title page therefor.

Insert drawing sheets containing figures 6-9.
Figures 6, 7, 8A, 8B, 8C, and 9, filed with the original application papers, were not printed in the patent, U.S. Patent No. 6,758,975 B2. Only Figures 1, 1A, 1B, 1C, 2, 3, 4, and 5, appear in the printed patent.

Signed and Sealed this

Thirty-first Day of August, 2010

David J. Kappos
*Director of the United States Patent and Trademark Office*

(12) United States Patent
Peabody et al.

(10) Patent No.: US 6,758,975 B2
(45) Date of Patent: Jul. 6, 2004

(54) AUTOMATED PERITONEAL DIALYSIS SYSTEM AND PROCESS WITH IN-LINE STERILIZATION OF DIALYSATE

(75) Inventors: Alan M. Peabody, Greenville, SC (US); Jeffrey J. Shimon, Mountain View, CA (US); Joel Frederic Jensen, Redwood City, CA (US)

(73) Assignee: Piedmont Renal Clinic, PA, Greenville, SC (US)

( * ) Notice: Subject to any disclaimer, the term of this patent is extended or adjusted under 35 U.S.C. 154(b) by 89 days.

(21) Appl. No.: 10/075,175

(22) Filed: Feb. 14, 2002

(65) Prior Publication Data

US 2002/0162778 A1 Nov. 7, 2002

Related U.S. Application Data

(60) Provisional application No. 60/269,570, filed on Feb. 16, 2001.

(51) Int. Cl.[7] ............................................. B01D 65/02
(52) U.S. Cl. ........................... 210/645; 73/38; 73/40; 210/85; 210/90; 210/257.2; 210/321.69; 210/739; 210/741; 604/29; 604/65
(58) Field of Search ........................... 210/85, 90, 97, 210/106, 108, 257.2, 258, 321.69, 321.71, 636, 645–647, 739, 741, 744; 73/38, 40, 40.5 R, 40.7; 134/22.1, 22.11, 22.12, 56 R; 604/29–31, 65, 4.01, 5.01

(56) References Cited

U.S. PATENT DOCUMENTS

| | | | |
|---|---|---|---|
| 3,825,493 A | 7/1974 | Brown et al. ................ 210/23 |
| 4,239,041 A | 12/1980 | Popovich et al. ........... 128/213 |
| 4,311,587 A | 1/1982 | Nose et al. ................. 210/136 |
| 4,311,687 A | 1/1982 | Hertl et al. ................. 210/136 |
| 4,586,920 A | 5/1986 | Peabody ..................... 604/29 |
| 4,718,890 A | 1/1988 | Peabody ..................... 604/29 |
| 4,747,822 A | 5/1988 | Peabody ..................... 604/29 |
| 5,004,459 A | 4/1991 | Peabody et al. ............. 604/29 |
| 5,643,201 A | 7/1997 | Peabody et al. ............. 604/31 |
| 5,683,584 A | 11/1997 | Wenthold et al. .......... 210/500 |
| 5,808,181 A | * 9/1998 | Wamsiedler et al. ......... 73/38 |
| 5,827,820 A | * 10/1998 | duMoulin et al. ........... 514/2 |
| 5,925,011 A | * 7/1999 | Faict et al. ................. 604/29 |
| 5,944,684 A | 8/1999 | Roberts et al. ............... 604/5 |
| 6,074,559 A | 6/2000 | Hahmann et al. .......... 210/645 |
| 6,254,567 B1 | * 7/2001 | Treu et al. .................. 604/29 |
| 6,280,632 B1 | * 8/2001 | Polaschegg ................ 210/739 |
| 6,635,179 B1 | * 10/2003 | Summerton et al. ........ 210/650 |

* cited by examiner

*Primary Examiner*—Joseph Drodge
(74) *Attorney, Agent, or Firm*—McNair Law Firm, PA; Cort Flint

(57) ABSTRACT

An automated peritoneal dialysis system for performing continuous peritoneal dialysis is disclosed which includes a fluid circuit for delivering unsterilized dialysate from an uninterrupted supply, and a dialysate sterilization component having at least one in-line sterilization filter assembly disposed in the inflow line segment for realtime sterilization of the unsterilized dialysate during flow prior to patient delivery. A filter test component is operatively associated with the sterilization filter assembly for conducting a realtime integrity test on the filter assembly to test for a filter failure which would allow contaminants into the dialysate prior to patient delivery. If the filter fails the test, the fluid is discarded. In this manner, sterilization of fluid in realtime during a peritoneal dialysis process provides a high rate of dialysate exchange during repeated dialysate fill and drain cycles.

64 Claims, 12 Drawing Sheets

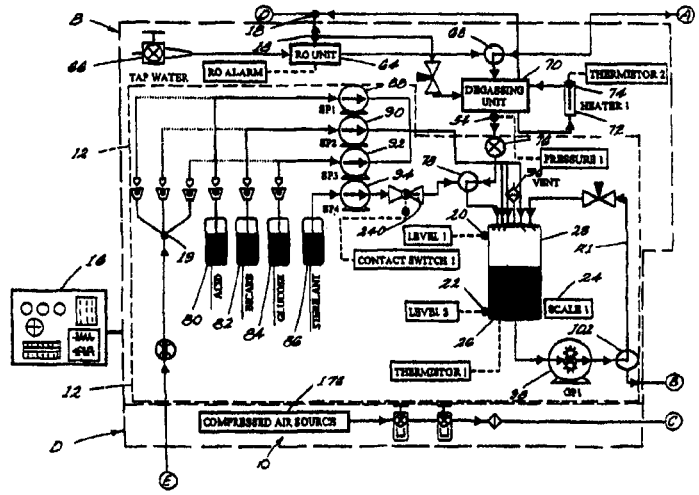

SYSTEM STERILIZATION MODE